(12) United States Patent
Hawkett et al.

(10) Patent No.: US 8,709,486 B2
(45) Date of Patent: Apr. 29, 2014

(54) ADMINISTRABLE COMPOSITIONS

(75) Inventors: Brian Stanley Hawkett, Mona Vale (AU); Nirmesh Jain, Paramatta (AU); Thi Thuy Binh Pham, Rydalmere (AU); Yanjun Wang, Evatt (AU); Gregory Goodman Warr, Earlwood (AU)

(73) Assignee: The University of Sydney, New South Wales (AU)

( * ) Notice: Subject to any disclaimer, the term of this patent is extended or adjusted under 35 U.S.C. 154(b) by 147 days.

(21) Appl. No.: 12/993,056

(22) PCT Filed: May 15, 2009

(86) PCT No.: PCT/AU2009/000620
§ 371 (c)(1),
(2), (4) Date: Feb. 9, 2011

(87) PCT Pub. No.: WO2009/137890
PCT Pub. Date: Nov. 19, 2009

(65) Prior Publication Data
US 2011/0129417 A1    Jun. 2, 2011

(30) Foreign Application Priority Data

May 16, 2008  (AU) ................................ 2008902427
Sep. 19, 2008  (AU) ................................ 2008904892

(51) Int. Cl.
*A61K 9/14*    (2006.01)
(52) U.S. Cl.
USPC ....................................................... 424/489
(58) Field of Classification Search
None
See application file for complete search history.

(56) References Cited

U.S. PATENT DOCUMENTS

| | | |
|---|---|---|
| 3,736,262 A | 5/1973 | Pirtle |
| 4,772,407 A | 9/1988 | Carlson |
| 5,427,767 A | 6/1995 | Kresse et al. |
| 2003/0059398 A1 | 3/2003 | Ranger et al. |
| 2004/0072784 A1 | 4/2004 | Sant et al. |
| 2004/0115433 A1 | 6/2004 | Elaissari et al. |
| 2005/0266394 A1 | 12/2005 | Hatton et al. |
| 2007/0264199 A1 | 11/2007 | Labhasetwar et al. |

FOREIGN PATENT DOCUMENTS

| | | |
|---|---|---|
| JP | 2006-328309 | 7/2006 |
| WO | WO 2004/081072 | 9/2004 |
| WO | WO 2007/097593 | 8/2007 |
| WO | WO 2007/112503 | 10/2007 |

OTHER PUBLICATIONS http://www.iupac.org/publications/pac/pdf/2010/pdf/8202x0483.pdf, accessed Sep. 20, 2013.*

(Continued)

*Primary Examiner* — Paul Dickinson
(74) *Attorney, Agent, or Firm* — Merchant & Gould P.C.

(57) ABSTRACT

The present invention relates to a composition suitable for administration to a subject, the composition comprising pharmacologically acceptable particulate material dispersed throughout a pharmacologically acceptable liquid carrier, the particulate material being maintained in the dispersed state by a steric stabilizer, wherein the steric stabilizer is a polymeric material comprising a steric stabilizing polymeric segment and an anchoring polymeric segment, one or both of which are derived from one or more ethylenically unsaturated monomers that have been polymerized by a living polymerization technique, wherein the steric stabilizing polymeric segment is different from the anchoring polymeric segment, and wherein the anchoring polymeric segment has an affinity toward the surface of the particulate material and secures the stabilizer to the particulate material.

23 Claims, 1 Drawing Sheet

(56) References Cited

OTHER PUBLICATIONS

Figure 1:
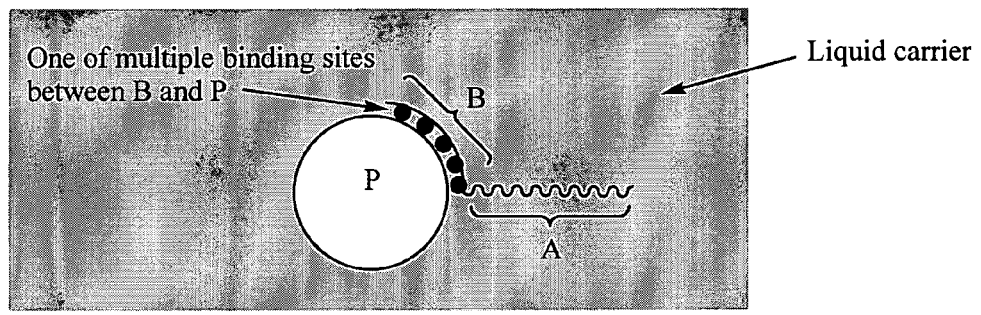

Arshady, "Microspheres for Biomedical Applications: Preparation of Reactive and Labelled Microspheres," *Biomaterials*, 14(1):5-15 (1993).
International Preliminary Report on Patentability for PCT/AU2009/000620 mailed Nov. 17, 2010.
International Search Report for PCT/AU2009/000620 mailed Jun. 23, 2009, 4 pgs.
Jordan et al., "Endocytosis of Dextran and Silan-Coated Magnetite Nanoparticles and the Effect of Intracellular Hyperthermia on Human Mammary Carcinoma Cells in vitro," *Journal of Magnetism and Magnetic Materials*, 194:185-96 (1999).
Kim et al., "Magnetomicelles: Composite Nanostructures from Magnetic Nanoparticles and Cross-Linked Amphiphilic Block Copolymers," *Nanoletters*, 5(10):1987-91 (2005).
Kim et al., "Starch-Coated Superparamagnetic Nanoparticles as MR Contrast Agents," *Chem. Mater.* 15:4343-51 (2003).
Liu et al., "Preparation of Magnetic Microspheres from Water-in-Oil Emulsion Stabilized by Block Copolymer Dispersant," *Biomacromolecules*, 6:1280-88 (2005).
Pich et al., "Temperature-Sensitive Hybrid Microgels with Magnetic Properties," *Langmuir*, 20:10706-10711 (2004).
Riess, "Micellization of Block Copolymers," *Progress in Polymer Science*, 28:1107-70 (2003).
Robinson et al., "Synthesis of Controlled-Structure Sulfate-Based Copolymers via Atom Transfer Radical Polymerisation and their Use as Crystal Habit Modifiers for $BaSO_4$," *Journal of Materials Chemistry*, 12:890-96 (2002).
Roux et al., "Steric Stabilization of Liposomes by pH-Responsive N-Isopropylacrylamide Copolymer," *Journal of Pharmaceutical Sciences*, 91(8):1795-1802 (2002).
Weissleder et al., "Long-Circulation Iron Oxides for MR Imaging," *Advanced Drug Delivery Reviews*, 16:321-34 (1995).
Japanese Office Action for JP 2011-508773 mailed Oct. 1, 2013.

\* cited by examiner

ADMINISTRABLE COMPOSITIONS

This application is a National Stage Application of PCT/AU2009/000620, filed 15 May 2009, which claims benefit of Serial No. 2008902427, filed 16 May 2008 in Australia and Serial No. 2008904892, filed 19 Sep. 2008 in Australia and which applications are incorporated herein by reference. To the extent appropriate, a claim of priority is made to each of the above disclosed applications.

FIELD OF THE INVENTION

The present invention relates to compositions suitable for administration to a subject, and in particular to an administrable composition comprising particulate material dispersed throughout a liquid carrier. The compositions in accordance with the invention are particularly suited for use as an administrable composition in imaging technology, and it will therefore be convenient to describe the invention with an emphasis toward this application. However, it is to be understood that the compositions may be used in various other medicinal or diagnostic applications.

BACKGROUND OF THE INVENTION

Compositions comprising particulate material dispersed throughout a liquid carrier suitable for administration to a subject (e.g. animal or human) have long been used in the field of medicine. For example, certain pharmaceutical agents may be provided in the form of an administrable composition in which the agent is dispersed or suspended throughout a liquid carrier. Contrast agents for imaging techniques are also typically provided in the form of an administrable composition in which the agent is dispersed or suspended throughout a liquid carrier.

In such compositions it is generally important that the dispersion remains stable (i.e. that the particulate material remains dispersed throughout the carrier liquid) at the very least up until the composition is to be administered. For example, a poorly formulated pharmaceutical dispersion might allow the pharmaceutical agent to settle out from the liquid carrier as sediment, thereby reducing the therapeutic concentration of the agent in the dispersion. This of course could result in under-dosing or over-dosing a patient, which may seriously compromise the patient's treatment.

The importance of the particulate material remaining in a dispersed state might also extend to after the composition has been administered to a subject. For example, it is particularly important that parenterally administered contrast agents remain in a dispersed state in vivo. In particular, flocculation of the contrast agent in vivo can be life-threatening to the subject.

Stabilisers are commonly employed to help maintain the particulate material in a dispersed state. The stabilisers typically function by (a) interacting with both the particulate material and the surrounding liquid environment (i.e. the liquid carrier of the composition or the liquid carrier in vivo), and (b) presenting electrostatic and/or steric repulsion forces that help maintain the particulate material in a dispersed state. A variety of such stabilisers of both natural and synthetic origin are known.

However, under certain circumstances it can be difficult to maintain particulate material in a dispersed state throughout a liquid carrier. For example, it is sometimes desirable or necessary to prepare administrable compositions comprising a liquid carrier having a relatively high ionic strength (e.g. an ionic strength comparable with that in vivo—isotonic). In that case, some stabilisers are simply ineffective in or perform poorly at providing a stable dispersion of the particulate material throughout the liquid carrier. This problem can also present itself post administration of the composition. In particular, liquid carriers presented to the particulate material in vivo can also have a relatively high ionic strength.

In addition to or separate from the effect a given liquid environment may have on a stabilisers ability to maintain the particulate material in a dispersed state, the concentration of the particulate material per se in the liquid environment can also impact on this ability. In particular, those skilled in the art will appreciate that there is typically an equilibrium set up between the interaction of conventional stabilisers with the particulate material and the surrounding liquid environment. Thus, as the volume of the surrounding liquid environment increases relative to a given stabilised particulate material, the equilibrium may shift in favour of the stabiliser spending more time associated with the liquid environment, thereby presenting greater opportunity for the particulate material to flocculate or simply fall out of dispersion. Although this equilibrium is reversed as the volume of surrounding liquid is reduced relative to a given stabilised particulate material (i.e. increased concentration of the particulate material in the surrounding liquid), many stabilisers nevertheless can not maintain particulate material in a dispersed and readily flowable state at concentrations above a modest 40 wt. %.

Such concentration effects can apply to the composition per se prior to its administration and/or to the composition once it has been administered. Those skilled in the art will appreciate that the dilution effect of administering a composition to a subject can be particularly problematic with regard to maintaining particulate material in a stabilised state in vivo for any practical length of time.

An opportunity therefore remains to address or ameliorate one or more disadvantages or shortcomings associated with existing administrable compositions, or to at least provide a useful alternative to conventional administrable compositions.

SUMMARY OF THE INVENTION

The present invention therefore provides a composition suitable for administration to a subject, the composition comprising pharmacologically acceptable particulate material dispersed throughout a pharmacologically acceptable liquid carrier, the particulate material being maintained in the dispersed state by a steric stabiliser, wherein the steric stabiliser is a polymeric material comprising a steric stabilising polymeric segment and an anchoring polymeric segment, one or both of which are derived from one or more ethylenically unsaturated monomers that have been polymerised by a living polymerisation technique, wherein the steric stabilising polymeric segment is different from the anchoring polymeric segment, and wherein the anchoring polymeric segment has an affinity toward the surface of the particulate material and secures the stabiliser to the particulate material.

Compositions in accordance with the invention have advantageously been found to exhibit particularly stable dispersions of particulate material at both high and low concentrations throughout a diverse array of liquid carriers, including those having a high ionic strength. Compositions in accordance with the invention can also advantageously be prepared using a variety of particulate materials having an organic and/or inorganic composition.

Upon administration to a subject, the compositions in accordance with the invention can also advantageously deliver the particulate material to the subject in a form that also enables the particulate material to be maintained in a dispersed state in vivo.

Figure 2:
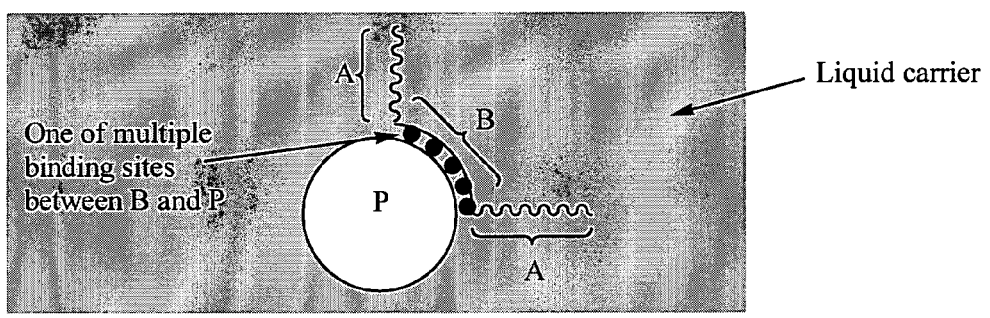

The present invention therefore also provides particulate material dispersed throughout an in vivo liquid carrier, the particulate material being maintained in the dispersed state by a steric stabiliser, wherein the steric stabiliser is a polymeric material comprising a steric stabilising polymeric segment and an anchoring polymeric segment, one or both of which are derived from one or more ethylenically unsaturated monomers that have been polymerised by living polymerisation technique, wherein the steric stabilising polymeric segment is different from the anchoring polymeric segment, and wherein the anchoring polymeric segment has an affinity toward the surface of the particulate material and secures the stabiliser to the particulate material.

Without wishing to be limited by theory, it is believed that the steric stabiliser used in accordance with the invention forms a strong association with the particulate material and provides for a particularly stable dispersion of the particulate material throughout a liquid carrier. The strong association between the particulate material and the steric stabiliser is believed to result from the polymeric nature of the anchoring segment of the stabiliser which provides multiple sites for binding interactions between the segment and the particulate material. The steric stabilising polymeric segment of the stabiliser is believed to enable the particulate material to be maintained in a dispersed state throughout a diverse array of liquid carriers by providing steric repulsive forces.

Without wishing to be limited by theory, it is also believed that by providing the steric stabiliser with steric stabilising and anchoring polymeric segments that are different, each polymeric segment can advantageously be tailored to, in the case of the steric stabilising segment, maximise steric stabilisation in a given liquid carrier, and, in the case of the anchoring segment, maximise securing the steric stabiliser to a given particulate material.

At least one of the steric stabilising and anchoring polymeric segments are derived from one or more ethylenically unsaturated monomers that have been polymerised by a living polymerisation technique. Employing at least one such segment is believed to enhance the stabilising properties of the steric stabiliser.

Compositions in accordance with the invention can advantageously be applied in a variety of medicinal, therapeutic and diagnostic applications. For example, where the particulate material is a pharmaceutically active agent (e.g. a drug), the compositions may be used to treat a disease or condition in a subject. Where the particulate material is a diagnostic agent (e.g. a contrast agent or radioactive isotope), the compositions in accordance with the invention may be used in diagnostic applications such as diagnostic imaging. Where the particulate material is a therapeutic agent (e.g. magnetic particles or radioactive isotope), the compositions in accordance with the invention may be used in therapeutic applications such as hyperthermia or radiation therapy.

The present invention therefore also provides a pharmaceutical composition suitable for administration to a subject, the composition comprising a pharmaceutical agent in the form of particulate material dispersed throughout a pharmacologically acceptable liquid carrier, the particulate material being maintained in the dispersed state by a steric stabiliser, wherein the steric stabiliser is a polymeric material comprising a steric stabilising polymeric segment and an anchoring polymeric segment, one or both of which are derived from one or more ethylenically unsaturated monomers that have been polymerised by a living polymerisation technique, wherein the steric stabilising polymeric segment is different from the anchoring polymeric segment, and wherein the anchoring polymeric segment has an affinity toward the surface of the particulate material and secures the stabiliser to the particulate material.

The present invention further provides a diagnostic composition suitable for administration to a subject, the composition comprising a diagnostic agent in the form of particulate material dispersed throughout a pharmacologically acceptable liquid carrier, the particulate material being maintained in the dispersed state by a steric stabiliser, wherein the steric stabiliser is a polymeric material comprising a steric stabilising polymeric segment and an anchoring polymeric segment, one or both of which are derived from one or more ethylenically unsaturated monomers that have been polymerised by a living polymerisation technique, wherein the steric stabilising polymeric segment is different from the anchoring polymeric segment, and wherein the anchoring polymeric segment has an affinity toward the surface of the particulate material and secures the stabiliser to the particulate material.

In one embodiment, the compositions in accordance with the invention are used to facilitate obtaining an image of a region of interest of a subject.

The present invention therefore also provides a method for providing an image of a region of interest of a subject, said method comprising administering to the subject a composition in accordance with the invention, and using diagnostic imaging technique to obtain the image of the region of interest. In that case the particulate material will generally be in the form of or comprise a diagnostic agent such as a contrast agent or radioactive isotope.

Compositions in accordance with the invention comprising dispersed diagnostic agent are expected to be particularly useful when employed in the field of ultrasound, X-ray, Computed Tomography (CT), Single Photon Emission Computed Tomography (SPECT), Positron Emission Tomography (PET) and Magnetic Resonance Imaging (MRI) techniques.

Medicinal applications for the administerable compositions of the invention are not only intended to embrace therapeutic treatments using pharmaceutical agents, but also therapeutic treatments using magnetic or radioactive particulate materials (e.g. for hyperthermia or radiation therapy).

The present invention therefore also provides a therapeutic composition suitable for administration to a subject, the composition comprising a therapeutic agent in the form of particulate material dispersed throughout a pharmacologically acceptable liquid carrier, the particulate material being maintained in the dispersed state by a steric stabiliser, wherein the steric stabiliser is a polymeric material comprising a steric stabilising polymeric segment and an anchoring polymeric segment, one or both of which are derived from one or more ethylenically unsaturated monomers that have been polymerised by a living polymerisation technique, wherein the steric stabilising polymeric segment is different from the anchoring polymeric segment, and wherein the anchoring polymeric segment has an affinity toward the surface of the particulate material and secures the stabiliser to the particulate material.

Further aspects of the invention appear below in the detailed description of the invention.

BRIEF DESCRIPTION OF THE DRAWINGS

The invention will also be described herein with reference to the following non-limiting drawings in which:

FIG. 1 presents a simplified schematic illustration not to scale showing: the multiple binding interactions between the anchoring polymeric segment (B) and the particulate material (P), and the steric stabilising segment (A) solubilised in the liquid carrier; and FIG. 2 presents a simplified schematic illustration not to scale showing: the multiple binding interactions between the anchoring polymeric segment (B) and the particulate material (P), and the steric stabilising segments (A) solubilised in the liquid carrier.

DETAILED DESCRIPTION OF THE INVENTION

Compositions in accordance with the invention are suitable for administration to a subject. By the term "subject" is meant either an animal or human subject. By "animal" is meant primates, livestock animals (including cows, horses, sheep, pigs and goats), companion animals (including dogs, cats, rabbits and guinea pigs), and captive wild animals (including those commonly found in a zoo environment). Laboratory animals such as rabbits, mice, rats, guinea pigs and hamsters are also contemplated as they may provide a convenient test system. In some embodiments, the subject is a human subject.

By the composition being "suitable" for administration to a subject is meant that administration of the composition to a subject will not result in unacceptable toxicity, including allergenic responses and disease states.

By "administration" of the composition to a subject is meant that the composition is presented such that the particulate material can be transferred to the subject. There is no particular limitation on the mode of administration, but this will generally be by way of oral, parenteral (including subcutaneous, intradermal, intramuscular, intravenous, intrathecal, and intraspinal), inhalation (including nebulisation), topical, rectal and vaginal modes.

The compositions in accordance with the invention comprise pharmacologically acceptable particulate material dispersed throughout a pharmacologically acceptable liquid carrier. By "pharmacologically acceptable" is meant that the particulate material, liquid carrier, or other constituent of the composition (e.g. the steric stabiliser) is suitable for administration to a subject in their own right. In other words, administration of the particulate material, liquid carrier or other constituent of the composition to a subject will not result in unacceptable toxicity, including allergenic responses and disease states.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Having said this, those skilled in the art will appreciate that the suitability of a composition for administration to a subject and whether or not a given particulate material or liquid carrier would be considered pharmacologically acceptable, will to some extent depend upon the mode of administration selected. Thus, the mode of administration may need to be considered when evaluating whether a given composition is suitable for administration to a subject or pharmacologically acceptable.

By the particulate material being "dispersed throughout" a liquid carrier is meant that the particulate material presents as a dispersed phase throughout the liquid carrier which itself, relative to the particulate material, presents as a continuous liquid medium or phase. In other words, the composition might be described as comprising a suspension or dispersion of the particulate material throughout the liquid carrier.

As used herein, the term "liquid" in the context of the liquid carrier is intended to mean a vehicle in which the particulate material is dispersed throughout and which is in a liquid state at least at the temperature of intended use of the compositions in accordance with the invention. Typically, a liquid carrier will be considered to be in a "liquid" state if, in the absence of a stabiliser, particulate material dispersed throughout the carrier can flocculate or settle out from the carrier to form a sediment. In other words, if the particulate material can move relatively freely in the vehicle, then it is considered "liquid".

The liquid carrier used in compositions of the invention may be made up of one or more different liquids. Suitable pharmacologically acceptable liquid carriers are described in Martin, Remington's Pharmaceutical Sciences, 18$^{th}$ Ed., Mack Publishing Co., Easton, Pa., (1990), and include, but are not limited to, liquids that may be sterilised such as water and oils, including those of petroleum, animal, vegetable, mineral or synthetic origin, such as peanut oil, soya bean oil, mineral oil, sesame oil, and the like. Other liquid carriers include methylene glycol, propylene glycol, polyethylene glycol, polypropylene glycol, ethanol, isopropyl alcohol, benzyl alcohol. Water or soluble saline solutions and aqueous dextrose and glycerol solutions are preferably employed as liquid carriers, particularly for injectable solutions.

The compositions of the invention may comprise one or more pharmacologically acceptable additives known to those in the art. For example, the liquid carrier may comprise one or more additives such as wetting agents, de-foaming agents, surfactants, buffers, electrolytes, preservatives, colourings, flavourings, and sweeteners.

Where the particulate material is a pharmaceutical agent, an additive included in the composition may be a pharmaceutical adjuvant in that the additive may improve the efficacy or potency of the agent.

The particular nature of the liquid carrier and any additive therein (if present) will in part depend upon the intended application of the composition. Those skilled in the art will be able to select a suitable liquid carrier and additive (if present) for the intended application of the composition.

The particulate material described herein (as part of the composition) may be administered in, as appropriate, a treatment, inhibitory, or diagnostic effective amount. A treatment, inhibitory, or diagnostic effective amount is intended to include an amount which, when administered according to the desired dosing regimen, achieves a desired therapeutic or diagnostic effect, including one or more of: alleviating the symptoms of, preventing or delaying the onset of, inhibiting or slowing the progression of, diagnosing, or halting or reversing altogether the onset or progression of a particular condition being treated and/or assessed.

Suitable dosage amounts and dosing regimens to achieve this can be determined by the attending physician and may depend on the particular condition being treated or diagnosed, the severity of the condition as well the general age, health and weight of the subject.

Dosing may occur at intervals of minutes, hours, days, weeks, months or years or continuously over any one of these periods. Suitable dosages of the particulate material per se may lie within the range of about 0.1 ng per kg of body weight to 1 g per kg of body weight per dosage. The dosage may be in the range of ~1 μg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

Compositions in accordance with the invention may be administered in a single dose or a series of doses.

Where the compositions in accordance with the invention are suitable for parenteral administration, they will generally be in the form of an aqueous or non-aqueous isotonic sterile injection solution that may contain one or more of an antioxidant, buffer, bactericide or solute which renders the composition isotonic with the blood of the intended subject. Such compositions may be presented in unit-dose or multi-dose sealed containers, for example, ampoules and vials.

Upon administration, compositions in accordance with the invention may be diluted in vivo. For example, dilution can occur when the composition is administered orally or parenterally. In that case, the liquid carrier of the composition may become so dilute in vivo that the surrounding liquid environment throughout which the particulate material is dispersed becomes more representative of an in vivo liquid (i.e. a biological liquid/fluid within the subject) than the original liquid carrier. For example, once administered orally, particulate material from the composition might more aptly be described as being dispersed throughout gastric fluid rather than the original liquid carrier of the composition. Once administered parenterally, the particulate material from the composition might more aptly be described as being dispersed throughout blood rather than the original liquid carrier of the composition. Under these circumstances, it will be convenient to refer to the particulate material as being dispersed throughout an in vivo liquid carrier (i.e. a biological liquid/fluid within the subject). With the exception of any compositional differences between a liquid carrier of compositions in accordance with the invention and an in vivo liquid carrier, matters described herein relating to the liquid carrier of the composition will also generally apply to an in vivo liquid carrier.

As used herein, the expression "particulate material" is intended to embrace any material having utility in medicinal/diagnostic applications that is capable of being dispersed throughout the liquid carrier and that presents a surface to which the stabiliser may be secured. Provided that it can be dispersed throughout the carrier liquid, the particulate material may take any shape or size. The size of a given particulate material will generally be dictated by the intended application of the composition. The largest dimension of the particulate material will generally be no greater than about 10 microns, preferably no greater than about 2 microns.

The compositions in accordance with the invention have been found to be particularly effective at forming a stable dispersion of sub-micron particles, for example, less than 0.5 microns, less than 0.25 microns, less than 0.1 microns, less than 0.01 microns, and even less than 0.005 microns. The particulate material is therefore intended to embrace colloidal material.

By having an ability to be dispersed throughout the liquid carrier, it will be appreciated that the particulate material will be sufficiently insoluble in the liquid carrier so as to enable the composition to have effective application. Thus, the particulate material may be substantially insoluble in the liquid carrier prior to administration, but exhibit at least a degree of solubility post administration, for example a degree of solubility in an in vivo liquid carrier. In this way, a pharmaceutically active particulate material may be released in vivo upon being administered to a subject.

The particulate material may be in the form of primary particles, or in the form or an aggregation of primary particles.

For avoidance of any doubt, reference herein to the "size" of the particulate material is intended to denote an average size of the particles based on the largest dimension of a given particle. Particulate material having a size of about 1 micron or more is to be determined by light microscopy, whereas particulate material having a size of less than about 1 micron is to be determined by Transmission Electron Microscopy (TEM).

For avoidance of any doubt, when the particulate material is in the form of an aggregation of primary particles, reference to the size of such material is intended to be a reference to the largest dimension of the aggregate not the primary particles that form the aggregate.

The particulate material will typically at least have an outer surface that is solid at temperatures typically experienced by the composition when used in its intended application. Taking into account temperatures that may be experienced by the compositions during use and storage prior to use in their intended application, at least the outer surface of the particulate material will generally be in a solid state up to at least about 40° C., preferably about 50° C. The particulate material may of course, and in some embodiments does, have such a solid state composition throughout (i.e. is solid particulate material).

Apart from having medicinal or diagnostic utility, there is no particular limitation on composition of the particulate material. The particulate material may have an organic composition or an inorganic composition or a combination thereof. The particulate material may be selected from or comprise a pharmaceutically active compound (e.g. a drug), a metal, a metal alloy, a metal salt, a metal complex, a metal oxide, a radioactive isotope and/or combinations thereof.

Suitable particulate materials may comprise gold, silver and salts, complexes or oxides thereof, calcium carbonate, barium sulphate, iron oxide, chromium oxide, cobalt oxide, manganese oxide, iron oxyhydroxide, chromium oxyhydroxide, cobalt oxyhydroxide, manganese oxyhydroxide, chromium dioxide, other transition metal oxides, radioactive isotopes selected from Auger-electron emitters, alpha emitters and beta emitters, and combinations thereof.

Examples of Auger-electron emitters include $^{51}$Cr, $^{67}$Ga, $^{71}$Ge, $^{75}$Se, $^{77}$Br, $^{80m}$Br, $^{99m}$Tc, $^{103}$Pd, $^{103m}$Rh, $^{111}$In, $^{113m}$In, $^{115m}$In, $^{117m}$Sn, $^{119}$Sb, $^{123}$I, $^{125}$I, $^{131}$Cs, $^{161}$Ho, $^{165}$Er, $^{193m}$Pt, $^{195m}$Pt, $^{201}$Tl and $^{203}$Pb.

Examples of alpha emitters include $^{211}$At and $^{213}$Bi.

Examples of beta emitters include: low-energy β emitters such as $^{191}$Os, $^{35}$S, $^{33}$P, $^{45}$Ca, $^{199}$Au, $^{169}$Er, $^{67}$Cu, $^{47}$Sc, $^{177}$Lu, $^{161}$Tb, and $^{105}$Rh; medium-energy β emitters such as $^{131}$I, $^{153}$Sm, $^{77}$As, $^{143}$Pr, $^{198}$Au, $^{159}$Gd, $^{10}$Pd, $^{186}$Re, $^{111}$Ag, and $^{149}$Pm; and high-energy β emitters such as $^{165}$Dy, $^{89}$Sr, $^{32}$P, $^{166}$Ho, $^{188}$Re, $^{114m}$In, $^{142}$Pr, $^{90}$Y, and $^{76}$As.

Examples of radioactive isotopes that may be used in radiation therapy include $^{32}$P, $^{153m}$S, $^{90}$U, $^{125}$I, $^{192}$Ir, $^{103}$Pd, $^{111}$In, $^{166}$Ho and $^{213}$Bi.

Examples of radioactive isotopes that may be used as a diagnostic agent include $^{99m}$Tc, $^{67}$Ga, $^{64}$Cu, $^{89}$Zr and $^{18}$F.

Where a radioactive isotope is to be used in accordance with the invention, the radionuclide(s) may be used as the particulate material per se or may be combined with one or more other suitable particulate materials. In other words, the particulate material may comprise one or more radioactive isotopes. For example, $^{67}$Ga may be used in a form where it is combined with iron oxide particulate material.

In some embodiments of the invention, it is preferred that the particulate material is magnetic. Magnetic particulate material that may be used in accordance with the invention will generally be of a size of less than 1 micron. Those skilled in the art will appreciate that the composition and/or size of the particles can influence their magnetic properties. The magnetic particulate material will generally exhibit ferromagnetic, ferrimagnetic or superparamagnetic properties.

The specific size of the magnetic particulate material used will generally be dictated by the intended application of the compositions. For some applications, it may be desirable for the magnetic particulate material to be of a size of less than about 500 nm, for example less than about 100 nm, or less than about 50 nm.

There is no particular limitation on the type of magnetic particulate material that may be used in accordance with the invention. Examples of suitable magnetic materials include, but are not limited to, iron, nickel, chromium, cobalt, oxides thereof or mixtures of any of these. Preferred iron oxide magnetic particulate materials include γ-ion oxide (i.e. γ-$Fe_2O_3$, also known as maghemite) and magnetite ($Fe_3O_4$).

In some applications, it may be desirable to use magnetic material that is superparamagnetic (i.e. nano-superparamagnetic particles). As used herein, the term "superparamagnetic" is intended to mean magnetic particles that do not have the following properties; (i) coercivity, (ii) remanence, or (iii) a hysteresis loop when the rate of change of an applied magnetic field is quasi static.

The magnetic material is preferably selected from ferrites of general formula $MO.Fe_2O_3$ where M is a bivalent metal such as Fe, Co, Ni, Mn, Be, Mg, Ca, Ba, Sr, Cu, Zn, Pt or mixtures thereof, or magnetoplumbite type oxides of the general formula $MO.6Fe_2O_3$ where M is a large bivalent ion, metallic iron, cobalt or nickel. Additionally, they could be particles of pure Fe, Ni, Cr or Co or oxides of these. Alternatively they could be mixtures of any of these.

In one embodiment, the magnetic particulate material is or comprises iron oxide such as magnetite ($Fe_3O_4$) or maghemite (γ-$Fe_2O_3$) with a particle size preferably less than 50 nm, for example between 1 and 40 nm.

Particulate material used in accordance with the invention may conveniently be prepared using techniques known in the art.

In accordance with the invention, the particulate material is maintained in the dispersed state by a steric stabiliser. By being "maintained" in this context is meant that in the absence of the steric stabiliser the particulate material would otherwise flocculate or settle out from the liquid carrier as sediment. In other words, the steric stabiliser functions to retain the particulate material in the dispersed state.

As a result of the particulate material being maintained in the dispersed state, an administerable composition in accordance with the invention is considered to provide a stable dispersion of the particulate material throughout the liquid carrier. In this context, a "stable" dispersion is considered to be one in which the dispersed particulate material does not aggregate to an undesirable extent over the expected shelf life of the composition. As a guide only, a stable dispersion might be considered as one in which the dispersed particulate material does not increase in size through aggregation by more than 20%, preferably 10%, more preferably 5%, most preferably 1%, as measured by dynamic light scattering, over about 12 months, or over about two weeks when the dispersion is diluted in a solution having high ionic strength, for example a 0.15 M NaCl solution.

In accordance with the invention, a steric stabiliser functions to maintain the particulate material in the dispersed state. By being a "steric" stabiliser is meant that stabilisation of the particulate material throughout the liquid carrier occurs as a result of steric repulsion forces. Having said this, the steric stabiliser may present electrostatic repulsion forces that also assist with stabilisation of the particulate material. However, those skilled in the art will appreciate that such electrostatic forces will provide little if any stabilising function in liquid carriers having a relatively high ionic strength. The steric stabilising function of the stabiliser used in accordance with the invention therefore plays an important role in enabling the particulate material to be maintained in a dispersed state throughout the liquid carrier.

The steric stabiliser used in accordance with the invention has a polymeric composition. There is no particular limitation on the molecular weight of the steric stabiliser, and this feature of the stabiliser may be dictated in part on the mode by which compositions in accordance with the invention are to be administered to a subject. The steric stabiliser may, for example, have a number average molecular weight of up to about 50,000.

In some embodiments of the invention, it may be preferable that the number average molecular weight of the steric stabiliser is less than about 30,000, or less than about 20,000, or less than about 10,000, or even less than about 5,000. The number average molecular weight of the steric stabiliser may also range from about 1,000 to about 3,000.

Steric stabilisers used in accordance with the invention having a relatively low number average molecular weight (e.g. less than about 5,000, preferably in the range of from about 1,000 to about 3,000) have been found to be effective at stabilising particulate material, particularly sub-micron particulate material (i.e. where the largest dimension of the particulate material is less than 1 micron).

Molecular weight values defined herein are those determined using gel permeation chromatography (GPC).

Steric stabilisers used in accordance with the invention have been found to exhibit highly efficient stabilising properties in that stabilisation of the particulate material can be achieved at both low and high concentrations of the particulate material in the liquid carrier. The steric stabilisers have also been found to give rise to stable dispersions of the particulate material throughout liquid carriers having a high ionic strength (such as 0.15 M NaCl solution, and even as high as in a saturated NaCl solution at room temperature) and over a wide pH range.

For certain applications of administerable compositions in accordance with the invention (e.g. parenterally administered compositions for imaging), it may be desirable that the administered particulate material (e.g. a contrast agent) has a small stabilising corona (i.e. the volume occupied around the particulate material by the stabiliser). The ability of steric stabilisers used in accordance with the invention to perform efficiently and effectively while having a relatively low number average molecular weight, makes them particularly suited for use in those applications that can benefit from the presence of a small stabilising corona.

Upon being administered to a subject, components of the composition in accordance with the invention taken in vivo will ultimately be metabolised and/or be excreted by the subject. In respect of the steric stabiliser, reducing its number average molecular weight can also advantageously facilitate this process.

The amount of steric stabiliser used relative to the particulate material will vary depending on the nature of the particulate material, particularly its size. For example, 1 g of 5 nm particulate material will require more stabiliser than 1 g of 1 micron particulate material due to its increased surface area. Those skilled in the art will be able to determine the required amount of stabiliser for a given particulate material.

At least one of the steric stabilising and anchoring polymeric segments that make up the steric stabiliser are derived from one or more ethylenically unsaturated monomers that have been polymerised by a living polymerisation technique.

Further detail regarding suitable living polymerisation techniques is discussed below. Where only one of the segments is derived in this manner, the other segment may be derived by any other conventional polymerisation technique known by those skilled in the art.

By "steric stabilising polymeric segment" is meant a segment or region of the steric stabiliser that is polymeric (i.e. formed by the polymerisation of at least one type of monomer) and that provides for the steric stabilising function of the steric stabiliser. For convenience, the steric stabilising polymeric segment may hereinafter be referred to as polymeric segment "A".

As alluded to above, the steric stabilising polymeric segment functions to stabilise the particulate material throughout the liquid carrier by providing steric repulsion forces.

By being polymeric, it will be appreciated that the steric stabilising segment comprises polymerised monomer residues. Thus, the segment will comprise polymerised monomer residues that give rise to the required steric stabilising properties. The polymerised monomer residues that make up the steric stabilising polymeric segment may be the same or different.

The steric stabilising polymeric segment may be substituted with a moiety (e.g. an optional substituent as herein defined), or contain a polymerised monomer residue, that gives rise to electrostatic stabilising properties.

In order to provide the desired steric stabilising effect, the steric stabilising polymeric segment will be soluble in at least the liquid carrier of the composition. Determining the solubility of a given steric stabilising polymeric segment in a given liquid carrier can readily be determined by simply preparing the polymeric segment in isolation and conducting a suitable solubility test in the chosen liquid carrier.

The steric stabiliser as a whole, may or may not be soluble in the given carrier liquid, but will nonetheless present a steric stabilising polymeric segment that is.

Those skilled in the art will have an understanding of polymeric materials that may be employed as the steric stabilising polymeric segment, as to the monomers that may be polymerised to form such polymers. For example, suitable polymeric materials include, but are not limited to, polyacrylamide, polyethylene oxide, polyhydroxyethylacrylate, poly N-isopropylacrylamide, polydimethylaminoethylmethacrylate, polyvinyl pyrrolidone and copolymers thereof. Thus, suitable monomers that may be used to form the stabilising polymeric segment include, but are not limited to, acrylamide, ethylene oxide, hydroxyethylacrylate, N-isopropylacrylamide, dimethylaminoethylmethacrylate, vinyl pyrrolidone and combinations thereof.

The particular steric stabilising polymeric segment used as part of the steric stabiliser will of course depend upon the nature of the liquid carrier. For example, if an aqueous liquid carrier is used, the steric stabilising polymeric segment should be soluble in the aqueous media. Those skilled in the art will be able to select an appropriate steric stabilising polymeric segment for the chosen liquid carrier.

By being able to select a specific steric stabilising polymeric segment independent of the anchoring polymeric segment, the steric stabilisers used in accordance with the invention can advantageously be tailor designed to suit a particular liquid carrier and thereby maximise the steric stabilising properties of the steric stabiliser.

A polymerisation technique may be used to prepare the steric stabilising segment. Living polymerisation techniques have been found particularly useful in preparing the steric stabilising polymeric segment. Those skilled in the art will appreciate that "living polymerisation" is a form of addition polymerisation whereby chain growth propagates with essentially no chain transfer and essentially no termination that give rise to dead polymer chains. By a "dead polymer chain" is meant one that can not undergo further addition of monomers.

In a living polymerization, typically all polymer chains are initiated at the start of the polymerization with minimal new chains being initiated in latter stages of the polymerization. After this initiation process, all the polymer chains in effect grow at the same rate. Characteristics and properties of a living polymerization generally include (i) the molecular weight of the polymer increases with conversion, (ii) there is a narrow distribution of polymer chain lengths (i.e. they are of similar molecular weight), and (iii) additional monomers can be added to the polymer chain to create block co-polymer structures. Thus living polymerisation enables excellent control over molecular weight, polymer chain architecture and polydispersity of the resulting polymer that can not be achieved with non-living polymerization methods.

Suitable living polymerisation techniques may be selected from ionic polymerisation and controlled radical polymerisation (CRP). Examples of CRP include, but are not limited to, iniferter polymerisation, stable free radical mediated polymerisation (SFRP), atom transfer radical polymerisation (ATRP), and reversible addition fragmentation chain transfer (RAFT) polymerisation.

Living ionic polymerisation is a form of addition polymerisation whereby the kinetic-chain carriers are ions or ion pairs. The polymerisation proceeds via anionic or cationic kinetic-chain carriers. In other words, the propagating species will either carry a negative or positive charge, and as such there will also be an associated counter cation or counter anion, respectively. For example, in the case of anionic polymerisation, the polymerisation may be conducted using a moiety represented as $I^-M^+$, where I represents an organo-anion (e.g. an optionally substituted alkyl anion) and M represents an associated countercation, or in the case of living cationic polymerisation, the moiety might be represented as $I^+M^-$, where I represents an organo-cation (e.g. an optionally substituted alkyl cation) and M represents an associated counteranion. Suitable moieties for conducting anionic and cationic living polymerisation are well known to those skilled in the art.

The living polymerisation technique may be a CRP technique.

Iniferter polymerisation is a well known form of CRP, and is generally understood to proceed by a mechanism illustrated below in Scheme 1.

Scheme 1: General mechanism of controlled radical polymerisation with iniferters.

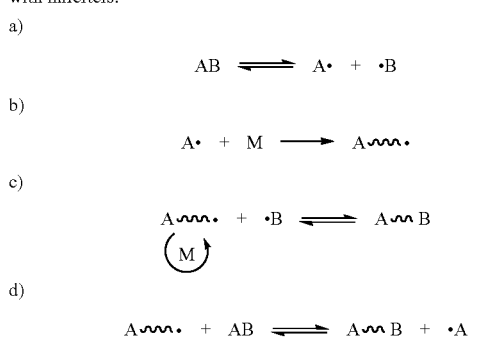

e)

f)

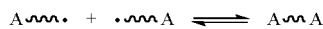

With reference to Scheme 1, the iniferter AB dissociates chemically, thermally or photochemically to produce a reactive radical species A and generally a relatively stable radical species B (for symmetrical iniferters the radical species B will be the same as the radical species A) (step a). The radical species A can initiate polymerisation of monomer M (in step b) and may be deactivated by coupling with radical species B (in step c). Transfer to the iniferter (in step d) and/or transfer to dormant polymer (in step e) followed by termination (in step f) characterise iniferter chemistry.

Suitable moieties for conducting iniferter polymerisation are well known to those skilled in the art, and include, but are not limited to, dithiocarbonate, disulphide, and thiuram disulphide moieties.

SFRP is a well known form of CRP, and is generally understood to proceed by a mechanism illustrated below in Scheme 2.

Scheme 2: General mechanism of controlled radical polymerisation with stable free radical mediated polymerisation.

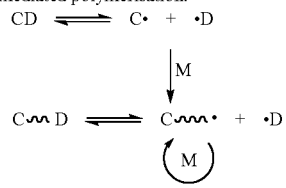

With reference to Scheme 2, SFRP moiety CD dissociates to produce an active radical species C and a stable radical species D. The active radical species C reacts with monomer M, which resulting propagating chain may recombine with the stable radical species D. Unlike iniferter moieties, SFRP moieties do not provide for a transfer step.

Suitable moieties for conducting SFRP are well known to those skilled in the art, and include, but are not limited to, moieties capable of generating phenoxy and nitroxy radicals. Where the moiety generates a nitroxy radical, the polymerisation technique is more commonly known as nitroxide mediated polymerisation (NMP).

Examples of SFRP moieties capable of generating phenoxy radicals include those comprising a phenoxy group substituted in the 2 and 6 positions by bulky groups such as tert-alkyl (e.g. t-butyl), phenyl or dimethylbenzyl, and optionally substituted at the 4 position by an alkyl, alkyloxy, aryl, or aryloxy group or by a heteroatom containing group (e.g. S, N or O) such dimethylamino or diphenylamino group. Thiophenoxy analogues of such phenoxy containing moieties are also contemplated.

SFRP moieties capable of generating nitroxy radicals include those comprising the substituent $R^1R^2N\!-\!O\!-\!$, where $R^1$ and $R^2$ are tertiary alkyl groups, or where $R^1$ and $R^2$ together with the N atom form a cyclic structure, preferably having tertiary branching at the positions α to the N atom. Examples of such nitroxy substituents include 2,2,5,5-tetraalkylpyrrolidinoxyl, as well as those in which the 5-membered hetrocycle ring is fused to an alicyclic or aromatic ring, hindered aliphatic dialkylaminoxyl and iminoxyl substituents. A common nitroxy substituent employed in SFRP is 2,2,6,6-tetramethyl-1-piperidinyloxy.

ATRP is a well known form of CRP, and generally employs a transition metal catalyst to reversibly deactivate a propagating radical by transfer of a transferable atom or group such as a halogen atom to the propagating polymer chain, thereby reducing the oxidation state of the metal catalyst as illustrated below in Scheme 3.

Scheme 3: General mechanism of controlled radical polymerisation with atom transfer radical polymerisation.

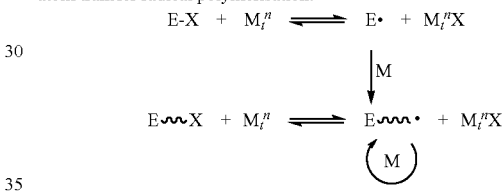

With reference to Scheme 3, a transferable group or atom (X, e.g. halide, hydroxyl, $C_1$-$C_6$-alkoxy, cyano, cyanato, thiocyanato or azido) is transferred from the organic compound (E) (e.g. optionally substituted alkyl, optionally substituted aryl, optionally substituted alkylaryl, or the polymer chain) to a transition metal catalyst ($M_t$, e.g. copper, iron, gold, silver, mercury, palladium, platinum, cobalt, manganese, ruthenium, molybdenum, niobium, or zinc) having oxidation number (n), upon which a radical species is formed that initiates polymerisation with monomer (M). As part of this process, the metal complex is oxidised ($M_t^{n+1}X$). A similar reaction sequence is then established between the propagating polymer chain and the dormant X end-capped polymer chains.

RAFT polymerisation is well known in the art and is believed to operate through the mechanism outlined below in Scheme 4.

Scheme 4: General mechanism of controlled radical polymerisation with reversible addition fragmentation chain transfer polymerisation.

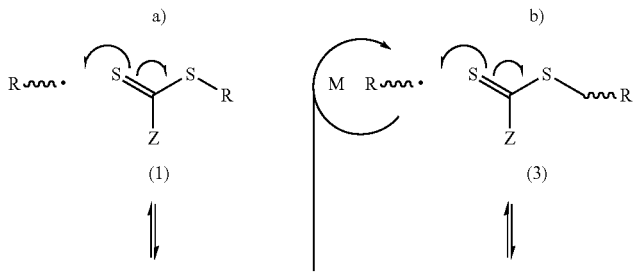

-continued

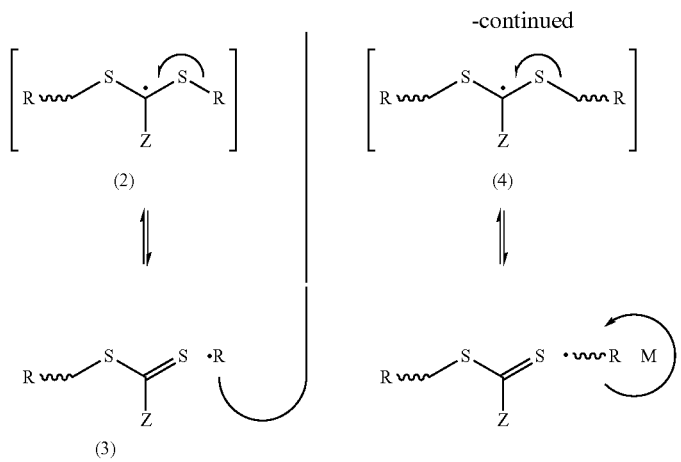

With reference to Scheme 4, RAFT polymerisation is believed to proceed through initial reaction sequence (a) that involves reaction of a RAFT moiety (1) with a propagating radical. The labile intermediate radical species (2) that is formed fragments to form a temporarily deactivated dormant polymer species (3) together a radical (R) derived from the RAFT moiety. This radical can then promote polymerisation of monomer (M), thereby reinitiating polymerisation. The propagating polymer chain can then react with the dormant polymer species (3) to promote the reaction sequence (b) that is similar to reaction sequence (a). Thus, a labile intermediate radical (4) is formed and subsequently fragments to form again a dormant polymer species together with a radical which is capable of further chain growth.

RAFT moieties generally comprise a thiocarbonylthio group (which is a divalent moiety represented by: —C(S)S—) and include xanthates, dithioesters, dithiocarbonates, dithiocarbanates and trithiocarbonates.

The steric stabilising polymeric segment may be formed by the polymerisation of one type of monomer or a combination of two or more different monomers. Accordingly, the steric stabilising polymeric segment may be a homopolymeric segment or a copolymeric segment.

Given that the stabilising polymeric segment forms only part of the steric stabiliser, rather than defining the steric stabilising polymeric segment in terms of its number average molecular weight, it can instead be useful to make reference to the number of polymerised monomeric units that collectively form the segment. Thus, although there is no particular limitation on the number of such units that collectively form the steric stabilising polymeric segment, in some embodiments of the invention it may be desirable that the steric stabiliser has a relatively low number average molecular weight. In that case, it is preferable that the steric stabilising polymeric segment has less than about 50, more preferably less than about 40, most preferably from about 10 to about 30 polymerised monomer residue units that make up the overall segment.

By an "anchoring polymeric segment" is meant a segment or region of the steric stabiliser that is polymeric and that has an affinity toward the surface of the particulate material and functions to secure the steric stabiliser to the particulate material. For convenience, the anchoring polymeric segment may hereinafter be referred to as polymeric segment "B".

By being polymeric, it will be appreciated that the anchoring segment comprises polymerised monomer residues. In particular, the segment will comprise polymerised monomer residues that give rise to the required binding affinity toward the particulate material. The polymerised monomer residues that make up the anchoring polymeric segment may be the same or different.

It is believed that the ability of the anchoring segment to present multiple sites for binding interactions with the particulate material at least in part gives rise to the excellent stabilising properties provided by the steric stabiliser.

Generally, the anchoring segment will have at least two polymerised monomer residues that each provides a site for binding with the particulate material, preferably at least three, more preferably at least five, still more preferably at least seven, most preferably at least ten of such polymerised monomer residues. Not all of the polymerised monomer residues that make up the anchoring segment are necessarily required to give rise to a binding interaction with the particulate material, but it is generally preferred that the majority if not all of the polymerised monomer residues that make up the anchoring segment do give rise to a binding interaction with the particulate material.

The anchoring segment may therefore be described as having multiple sites that collectively secure the stabiliser to the particulate material.

The anchoring polymeric segment can also be substituted with a moiety (e.g. an optional substituent as herein defined) that may or may not give rise to a binding interaction with the particulate material.

In order to provide the desired anchoring effect, the anchoring polymeric segment will have a binding affinity toward the particulate material. The specific mode by which the anchoring segments binds to the particulate material is not particularly important, for example it might be by way of electrostatic forces, hydrogen bonding, ionic charge, Van der Waals forces, or any combination thereof. A particular advantage provided by the anchoring polymeric segment is that it can provide multiple sites for binding interactions with the particulate material. Thus, even where a given binding site only provides a relatively weak interaction with the particulate material, the presence of multiples of such sites within the segment enables it as a whole to bind securely with the particulate material.

The specific anchoring polymeric segment required will generally be dictated by the nature of the particulate material to which it is to bind. When describing the interaction of the anchoring polymeric segment with the particulate material, it can be convenient to refer to the hydrophilic and hydrophobic character of the segment and the particulate material. Thus, in general, suitable binding interactions will occur when the segment and the particulate material have similar hydrophilic or hydrophobic character. For example, where the particulate material has a relatively hydrophilic surface (e.g. its surface can be wetted with an aqueous solution), then good binding should be attained using an anchoring polymeric segment that has hydrophilic character (e.g. in its isolated form the segment would be soluble in an aqueous medium). Such an example might be realised where the particulate material is of a type that can form a charge on its surface. In that case, it may be desirable for the segment to comprise polymerised residues of monomers that can also form a charge (e.g. residues of an ionisable monomer) so as to promote ionic binding between the segment and the particulate material. Promoting the formation of such charged species might be facilitated by adjusting the pH of the liquid carrier in which the stabiliser and particulate material reside.

By the term "ionisable monomer" is meant that the monomer comprises a functional group which can be ionised in solution to form a cationic or anionic group. Such functional groups will generally be capable of being ionised under acidic or basic conditions through loss or acceptance of a proton. Generally, the functional groups are acid groups or basic groups (i.e. groups that can donate or accept a H atom, respectively). For example, a carboxylic acid functional group may form a carboxylate anion under basic conditions, and an amine functional group may form a quaternary ammonium cation under acidic conditions. The functional groups may also be capable of being ionised through an ion exchange process.

Examples of suitable ionisable monomers having acid groups include, but are not limited to, methacrylic acid, acrylic acid, itaconic acid, p-styrene carboxylic acids, p-styrene sulfonic acids, vinyl sulfonic acid, vinyl phosphonic acid, monoacryloxyethyl phosphate, 2-(methacryloyloxy) ethyl phosphate, ethacrylic acid, alpha-chloroacrylic acid, crotonic acid, fumaric acid, citraconic acid, mesaconic acid, and maleic acid. Examples of suitable ionisable monomers which have basic groups include, but are not limited to, 2-(dimethyl amino) ethyl and propyl acrylates and methacrylates, and the corresponding 3-(diethylamino) ethyl and propyl acrylates and methacrylates.

Those skilled in the art will be able to select an appropriate anchoring polymeric segment to bind with the surface of a given particulate material.

By being able to select a specific anchoring polymeric segment independent of the steric stabilising polymeric segment, the steric stabilisers used in accordance with the invention can advantageously be tailor designed to suit a particular particulate material and thereby maximise the anchoring properties of the steric stabiliser. For example, it may be desirable that the anchoring polymeric segment comprise carboxylic acid, phosphinate, phosphonate and/or phosphate functional groups. Where the particulate material to which anchoring segment binds comprises iron (e.g. magnetic iron oxide particulate material), it may be desirable for the segment to comprise phosphinate, phosphonate, and/or phosphate functional groups. Such segments will generally be formed using monomers that comprise the phosphorous functional groups.

Those skilled in the art will appreciate the variety of polymeric materials that may be employed as the anchoring polymeric segment, as to the monomers that may be polymerised to form such polymers. For example, suitable polymeric materials include, but are not limited to, polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, the corresponding poly-3-(diethylamino) ethyl and propyl acrylates and methacrylates, hydrophobic acrylate and methacrylate polymers, polydimethylaminoethylmethacrylate, and copolymers thereof. Thus, suitable monomers that may be used to form the anchoring polymeric segment include, but are not limited to, acrylic acid, methacrylic acid, itaconic acid, p-styrene carboxylic acids, p-styrene sulfonic acids, vinyl sulfonic acid, vinyl phosphonic acid, monoacryloxyethyl phosphate, 2-(methylacryloyloxy) ethyl phosphate, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, the corresponding 3-(diethylamino) ethyl and propyl acrylates and methacrylates, styrene, hydrophobic acrylate and methacrylate monomers, dimethylaminoethylmethacrylate, and combinations thereof.

Living polymerisation techniques such as those herein described have been found particularly useful in preparing the anchoring polymeric segment. At least one of the steric stabilising and anchoring polymeric segments are derived from one or more ethylenically unsaturated monomers that have been polymerised by a living polymerisation technique. Where only one of the segments is derived in this manner, it will preferably be the anchoring segment.

The anchoring polymeric segment may be formed by the polymerisation of one type of monomer or a combination of two or more different monomers. Accordingly, the anchoring polymeric segment may be a homopolymeric segment or a copolymeric segment.

Given that the anchoring polymeric segment forms only part of the steric stabiliser, rather than defining the anchoring polymeric segment in terms of its number average molecular weight, it can instead be useful to make reference to the number of polymerised monomeric units that collectively form the segment. Thus, although there is no particular limitation on the number of such units that collectively form the anchoring polymeric segment, in some embodiments of the invention it may be desirable that the steric stabiliser has a relatively low number average molecular weight. In that case, it is preferable that the anchoring polymeric segment has less than about 50, more preferably less than about 40, still more preferably less than about 30, even more preferably from about 5 to about 25, most preferably from about 5 to about 15 polymerised monomer residue units that make up the overall segment.

When selecting the steric stabilising and anchoring polymeric segment, or the monomers that may be used to prepare them, it may be desirable to consider the properties of the respective polymeric segments in the context of the intended application of the composition. For example, one or both polymeric segment may be selected such that they are biodegradable and/or biocompatible.

Provided that the stabiliser functions as herein described there is no particular limitation on how the stabilising polymeric segment and the anchoring polymeric segment are to be spatially arranged.

The steric stabilising polymeric segment and the anchoring polymeric segment may be coupled to each other by any suitable means to form the steric stabiliser used in accordance with invention. For example, the steric stabiliser may be described as or comprising the structure A-C-B, where A represents the steric stabilising polymeric segment, B represents the anchoring polymeric segment and C represents a coupling moiety. Alternatively, the steric stabilising polymeric segment and the anchoring polymeric segment may be directly coupled to each other via a covalent bond and therefore the stabiliser can be simplistically described as or comprising an A-B block copolymer. In that case, A represents the steric stabilising polymeric segment and B represents the anchoring polymeric segment.

It will be appreciated from the description above that each of A and B can independently be a homopolymer or a copolymer (e.g. random, block, tapered, etc.). The stabiliser may comprise more than one steric stabilising polymeric segment (A) and more than one anchoring polymeric segment (B). For example, the stabiliser may be described as or comprising an A-B-A block copolymer. In that case, each A represents the steric stabilising polymeric segment, which may be the same or different, and B represents the anchoring polymeric segment. The stabiliser might also be described as or comprising a B-A-B block copolymer, where each B represents the anchoring polymeric segment, which may be the same or different, and A represents the steric stabilising polymeric segment that is of sufficient chain length such that it forms a "loop" that extends into the liquid carrier and performs its stabilising role.

The stabiliser may also have more complex structures such as star and comb polymer structures. In that case, the anchoring polymeric segment B might represent the main polymer backbone of such structures, with multiple steric stabilising polymeric segments A being attached thereto.

The interaction of a steric stabiliser used in accordance with the invention (in the form of an A-B block copolymer structure) with particulate material in the liquid carrier might be illustrated in the not to scale simplified schematic shown in FIG. 1.

With reference to FIG. 1, the steric stabiliser represented by an A-B block copolymer exhibits an affinity toward the surface of the particulate material (P) through the anchoring polymeric segment (B). The anchoring polymeric segment (B) therefore secures the steric stabiliser to the particulate material. The anchoring polymeric segment (B) provides multiple sites for binding interactions between the segment and the particulate material. The steric stabilising polymeric segment (A), which is different to segment (B), is soluble in the liquid carrier and functions to maintain the particulate material dispersed throughout the liquid carrier. It will be appreciated that in practice the surface of the particulate material will have many steric stabilisers secured thereto, and that these have been omitted from the illustration in FIG. 1 for clarity.

A similar illustration to that in FIG. 1 is shown in FIG. 2 where the steric stabiliser used in accordance with the invention is in the form of an A-B-A block copolymer.

At least one of the steric stabilising and anchoring polymeric segments are derived from one or more ethylenically unsaturated monomers that have been polymerised by a living polymerisation technique such as ionic polymerisation, iniferter polymerisation, SFRP, ATRP, and RAFT polymerisation. Of these living polymerisation techniques, RAFT polymerisation is preferred.

As discussed above, RAFT polymerisation is a well known radical polymerisation technique that enables polymers to be prepared having a well defined molecular architecture and a low poly dispersity. RAFT polymerisation is conducted using a RAFT moiety or agent, and polymers formed under the control of the RAFT agent (i.e. polymerised via a RAFT mechanism to form polymer) may be conveniently referred to as a "RAFT polymer" or a "RAFT derived polymer".

In one embodiment of the invention, the steric stabiliser is a RAFT derived polymer.

Those skilled in the art will appreciate that RAFT agents are commonly depicted as having the general structure Z—C(S)—S—R, and that upon formation a RAFT derived polymer will comprise the reaction residue of the RAFT agent. A steric stabiliser used in accordance with the invention might therefore have a structure depicted by general formula (I):

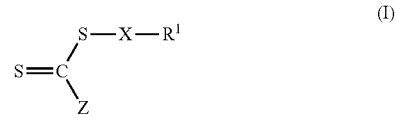

where X represents alone or in conjunction with $R^1$ or Z the polymeric structure of the steric stabiliser (e.g. having a A-B or A-B-A block copolymer structure etc as hereinbefore described), $R^1$ and Z are groups derived from the RAFT agent used in preparing the steric stabiliser and are independently selected such that it can function as a RAFT agent in the polymerisation of the monomers that give rise to X.

Where $R^1$ or Z functions as part of the steric stabiliser, it will generally function as the steric stabilising polymeric segment, in which case X will represent the anchoring polymeric segment. In such an embodiment, $R^1$ or Z will present steric stabilising properties as herein described, and X will be an anchoring polymeric segment as herein described that has been formed by RAFT polymerisation.

In order to function as a RAFT agent in the polymerisation of the one or more ethylenically unsaturated monomers, those skilled in the art will appreciate that $R^1$ will typically be an organic group that functions as a free radical leaving group under the polymerisation conditions employed and yet, as a free radical leaving group, retains the ability to reinitiate polymerisation. Similarly, those skilled in the art will appreciate that Z will typically be an organic group that functions to give a suitably high reactivity of the C=S moiety in the RAFT agent towards free radical addition without slowing the rate of fragmentation of the RAFT-adduct radical to the extent that polymerisation is unduly retarded.

Examples of suitable $R^1$ groups include alkyl, alkylaryl, alkoxyaryl, alkoxyheteroaryl, and a polymer chain, each of which is optionally substituted with one or more hydrophilic groups.

More specific examples of suitable $R^1$ groups can include $C_1$-$C_6$ alkyl, $C_1$-$C_6$ alkoxy aryl or heteroaryl, and a polymer chain selected from polyalkylene oxide polymers such as water soluble polyethylene glycol or polypropylene glycol, and alkyl end capped derivatives thereof, each of which is optionally substituted with one or more hydrophilic groups selected from —$CO_2H$, —$CO_2RN$, —$SO_3H$, —$OSO_3H$, —SORN, —$SO_2RN$, —$OP(OH)_2$, —$P(OH)_2$, —$PO(OH)_2$, —OH, —ORN, —$(OCH_2$—$CHR)_w$—OH, —$CONH_2$, CONHR', CONR'R", —NR'R", —$N^+$R'R"R'", where R is selected from $C_1$-$C_6$ alkyl, w is 1 to 10, R', R" and R'" are independently selected from alkyl and aryl which are optionally substituted with one or more hydrophilic substituents selected from —$CO_2H$, —$SO_3H$, —$OSO_3H$, —OH, —$(COCH_2CHR)_w$—OH, —$CONH_2$, —SOR and $SO_2R$, and salts thereof, R and w are as defined above. Preferred R' groups include, but are not limited to, —$CH(CH_3)CO_2H$, —$CH(CO_2H)CH_2CO_2H$, —$C(CH_3)_2CO_2H$, —$CH(CH_3)$ $CO_2(CH_2CH_2O)_nH$ and $—CH(CH_3)CO_2(CH_2CH_2O)_nCH_3$, where n is ranges from about 5 to about 50, or from about 10 to about 25.

Suitable Z groups may be selected from optionally substituted alkoxy, optionally substituted aryloxy, optionally substituted alkyl, optionally substituted aryl, optionally substituted heterocyclyl, optionally substituted arylalkyl, optionally substituted alkylthio, optionally substituted arylalkylthio, dialkoxy- or diaryloxy-phosphinyl [—P(=O)OR$^2_2$], dialkyl- or diaryl-phosphinyl [—P(=O)R$^2_2$], optionally substituted acylamino, optionally substituted acylimino, optionally substituted amino, $R^1—(X)—S—$ and a polymer chain, for example one selected from polyalkylene oxide polymers such as water soluble polyethylene glycol or polypropylene glycol, and alkyl end capped derivatives thereof, where $R^1$ and X are as defined above and $R^2$ is selected from optionally substituted $C_1$-$C_{18}$ alkyl, optionally substituted $C_2$-$C_{18}$ alkenyl, optionally substituted aryl, optionally substituted heterocyclyl, optionally substituted aralkyl, and optionally substituted alkaryl. Preferred Z groups include, but are not limited to, —$CH_2(C_6H_5)$, $C_1$-$C_{20}$ alkyl,

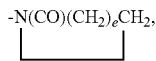

where e is 2 to 4, and —$SR^3$, where $R^3$ is selected from $C_1$ to $C_{20}$ alkyl. Preferred optional substituents for $R^2$ and Z groups include epoxy, hydroxy, alkoxy, acyl, acyloxy, carboxy (and salts), sulfonic acid (and salts), alkoxy- or aryloxy-carbonyl, isocyanato, cyano, silyl, halo, and dialkylamino.

In selecting both $R^1$ and Z groups of formula (I), all combinations of preferred $R^1$ and Z groups are also preferred.

Where the hydrophilic group is —$N^+R'R''R'''$ there will be an associated counter anion.

$R^1$ may also be an organic group optionally substituted with one or more hydrophobic groups. In that case, Z is preferably an organic group optionally substituted with one or more hydrophilic groups.

As used herein, the terms "aryl" and "heteroaryl" refer to any substituent which includes or consists of one or more aromatic or heteroaromatic ring respectively, and which is attached via a ring atom. The rings may be mono or polycyclic ring systems, although mono or bicyclic 5 or 6 membered rings are preferred. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, benzofuran, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted.

In this specification "optionally substituted" means that a group may or may not be further substituted with one or more groups selected from, but not limited to, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, acetyleno, carboximidyl, haloaryloxy, isocyano, cyano, formyl, carboxyl, nitro, nitroalkyl, nitroalkenyl, nitroalkynyl, nitroaryl, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphonyl, arylsulphonyl, alkylsolphinyl, arylsulphinyl, carboalkoxy, alkylthio, benzylthio, acylthio, sulphonamido, sulfanyl, sulfo and phosphorus-containing groups such as phosphate, phosphite and phosphate, alkoxysilyl, silyl, alkylsilyl, alkylalkoxysilyl, phenoxysilyl, alkylphenoxysilyl, alkoxyphenoxysilyl, arylphenoxysilyl, allophanyl, guanidino, hydantoyl, ureido, and ureylene.

Unless stated otherwise, the terms "halogen" and "halo" used herein refer to I, Br, Cl and F.

In this specification the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein, the term "salt" denotes a species in ionised form, and includes both acid addition and base addition salts. In the context of forming a RAFT polymer, suitable salts are those that do not interfere with the RAFT chemistry.

As used herein, the term "counter anion" denotes a species capable of providing a negative charge to balance the charge of the corresponding cation. Examples of counter anions include, Cl$^-$, I$^-$, Br$^-$, F$^-$, NO$_3^-$, CN$^-$ and PO$_3^-$.

As used herein, the term "alkoxy" denotes straight chain or branched alkoxy, preferably $C_{1-20}$ alkoxy. Examples of alkoxy include methoxy, ethoxy, n-propoxy, isopropoxy and the different butoxy isomers.

As used herein, the term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein, the term "alkynyl" denotes groups formed from straight chain, branched or cyclic alkyne including those structurally similar to the alkyl and cycloalkyl groups as previously defined, preferably $C_{2-20}$ alkynyl. Examples of alkynyl include ethynyl, 2-propynyl and 2- or 3-butynyl.

As used herein, the term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

As used herein, the terms "heterocyclic", "heterocyclyl" and "heterocycle" used on their own or as part of a term such as "heterocyclicalkenoyl", heterocycloxy" or "haloheterocyclyl" refer to aromatic, pseudo-aromatic and non-aromatic rings or ring systems which contain one or more heteroatoms selected from N, S, and O and which may be optionally substituted. Preferably the rings or ring systems have 3 to 20 carbon atoms. The rings or ring systems may be selected from those described above in relation to the definition of "heteroaryl".

Preferred steric stabilisers of formula (I) include, but are not limited to, the following general formulae (II) to (X):

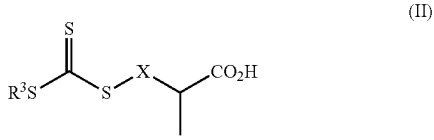

(II)

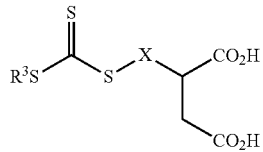

(III)

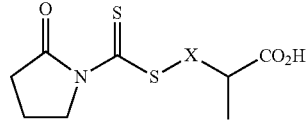

(IV)

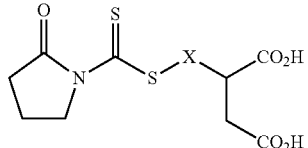

(V)

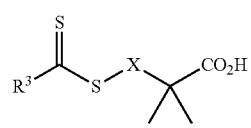

(VI)

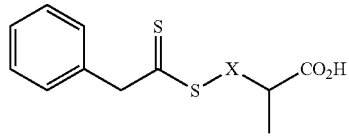

(VII)

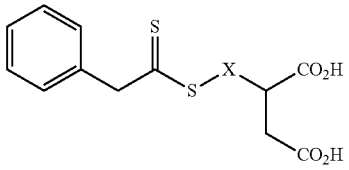

(VIII)

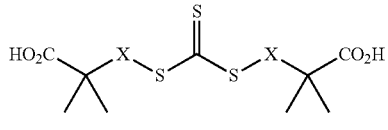

(IX)

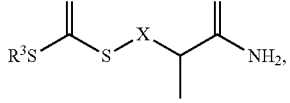

(X)

structures (II) to (IX) wherein one or both —$CO_2H$ group(s) in each structure is replaced by —$CH(CH_3)CO_2$ $(CH_2CH_2O)_n$ H or —$CH(CH_3)CO_2(CH_2CH_2O)_nCH_3$, structures (II), (III), (VI) and (X) wherein $R^3$ is replaced by —CH $(CH_3)CO_2(CH_2CH_2O)_n$H or —$CH(CH_3)CO_2(CH_2CH_2O)_n$ $CH_3$, structures (VII) and (VIII) wherein $PhCH_2$— is replaced by —$CH(CH_3)CO_2(CH_2CH_2O)_n$H or —$CH(CH_3)$ $CO_2(CH_2CH_2O)_n$ $CH_3$, and structures (IV) and (V) wherein the 5-membered nitrogen heterocycle is replaced by —CH $(CH_3)CO_2(CH_2CH_2O)_n$H or —$CH(CH_3)CO_2(CH_2CH_2O)_n$ $CH_3$, where n is ranges from about 5 to about 50, or from about 10 to about 25, where $R^3$ and X are as previously defined.

Where the Z—C(S)—S— and $R^1$-moieties of general formula (I) are not particularly important with respect to providing the steric stabiliser used in accordance with the invention with its advantageous properties, one or both of these moieties (or part thereof) may be removed or modified using techniques known in the art. There are numerous techniques known to remove or modify the Z—C(S)—S— moiety or part thereof from RAFT derived polymers (e.g. the removal of the sulphur containing groups). For example, the RAFT derived polymer may be reacted with benzoyl peroxide.

Preparing a steric stabiliser by RAFT polymerisation may involve polymerising under the control of a RAFT agent (i) one or more type of ethylenically unsaturated monomer to provide for at least one steric stabilising polymeric segment (A), and (ii) one or more type of different monomers to provide for at least one anchoring polymeric segment (B) (i.e. where A and B collectively form X in structure (I)). Alternatively, a steric stabiliser prepared by RAFT polymerisation may involve polymerising under the control of a RAFT agent (i) one or more type of ethylenically unsaturated monomer to provide for at least one steric stabilising polymeric segment (A), or (ii) one or more type of different monomers to provide for at least one anchoring polymeric segment (B) (i.e. where only one of A and B form X in structure (I) and $R^1$ in effect represents the other). Techniques, conditions and reagents known by those skilled in the art of RAFT polymerisation may be conveniently used to prepare such stabilisers precursors.

Suitable RAFT agents for preparing the steric stabiliser include, but are not limited to, those of general formula (IA):

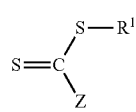
(IA)

where $R^1$ and Z are as previously defined.

In selecting both $R^1$ and Z groups for RAFT agents of the formula (IA), those agents resulting from the combination of preferred $R^1$ and Z groups are also preferred Preferred RAFT agents for preparing the steric stabilisers include, but are not limited to, those represented by the following general formulas (XI) to (IV):

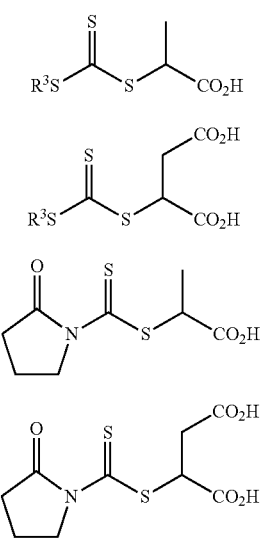
(XI)

(XII)

(XIII)

(XIV)

-continued

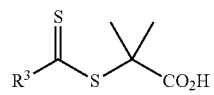
(XV)

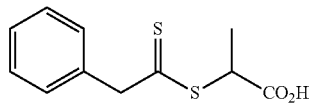
(XVI)

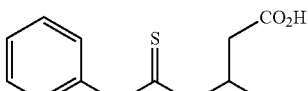
(XVII)

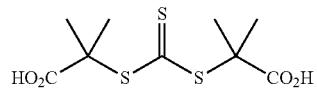
(XVIII)

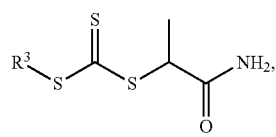
(IXX)

structures (XI) to (XVIII) wherein one or both —$CO_2H$ group(s) in each structure is replaced by —$CH(CH_3)CO_2(CH_2CH_2O)_nH$ or —$CH(CH_3)CO_2(CH_2CH_2O)_nCH_3$, structures (XI), (XII), (XV) and (IXX) wherein $R^3$ is replaced by —$CH(CH_3)CO_2(CH_2CH_2O)_nH$ or —$CH(CH_3)CO_2(CH_2CH_2O)_nCH_3$, structures (XVI) and (XVII) wherein $PhCH_2$— is replaced by —$CH(CH_3)CO_2(CH_2CH_2O)_nH$ or —$CH(CH_3)CO_2(CH_2CH_2O)_nCH_3$, and structures (XIII) and (XIV) wherein the 5-membered nitrogen heterocycle is replaced by —$CH(CH_3)CO_2(CH_2CH_2O)_nH$ or —$CH(CH_3)CO_2(CH_2CH_2O)_nCH_3$, where n is ranges from about 5 to about 50, or from about 10 to about 25, where $R^3$ and X are as previously defined.

When preparing a block copolymer structure of the steric stabiliser by any polymerisation technique, including RAFT polymerisation, those skilled in the art will also appreciate that each segment can be formed sequentially by the polymerisation of appropriate monomers. Alternatively, a preformed polymer may be employed as one of the segments and the other segment may be grafted thereto by the polymerisation of appropriate monomers.

Having regard to the discussion above concerning the required attributes of monomers that may be used to prepare the polymeric matrix of the beads and the steric stabilising and anchoring polymeric segments, suitable monomers that may be used in general are those which can be polymerised by a free radical process. Suitable monomers should also be capable of being polymerised with other monomers. The factors which determine copolymerisability of various monomers are well documented in the art. For example, see: Greenlee, R. Z., in Polymer Handbook $3^{rd}$ Edition (Brandup, J., and Immergut. E. H. Eds) Wiley: New York, 1989 p II/53.

Such monomers, including those mentioned above, may be selected from those with the general formula (XX):

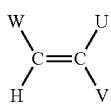

(XX)

where U and W are independently selected from the group consisting of —CO$_2$H, —CO$_2$R$^1$, —COR$^1$, —CSR$^1$, —CSOR$^1$, —COSR$^1$, —CONH$_2$, —CONHR$^1$, —CONR$^1$$_2$, hydrogen, halogen and optionally substituted C$_1$-C$_4$ alkyl, or U and W form together a lactone, anhydride or imide ring that may itself be optionally substituted, wherein the substituents are independently selected from the group consisting of hydroxy, —CO$_2$H, —CO$_2$R$^1$, —COR$^1$, —CSR$^1$, —CSOR$^1$, —COSR$^1$, —CN, —CONH$_2$, —CONHR$^1$, —CONR$^1$$_2$, —OR$^1$, —SR$^1$, —O$_2$CR$^1$, —SCOR$^1$, and —OCSR$^1$; and V is selected from the group consisting of hydrogen, R$^2$, —CO$_2$H, —CO$_2$R$^2$, —COR$^2$, —CSR$^2$, —CSOR$^2$, —COSR$^2$, —CONH$_2$, —CONHR$^2$, —CONR$^2$$_2$, —OR$^2$, —SR$^2$, —O$_2$CR$^2$, —SCOR$^2$, and —OCSR$^2$;

where R$^2$ is selected from the group consisting of optionally substituted C$_1$-C$_{18}$ alkyl, optionally substituted C$_2$-C$_{18}$ alkenyl, optionally substituted aryl, optionally substituted heteroaryl, optionally substituted carbocyclyl, optionally substituted heterocyclyl, optionally substituted aralkyl, optionally substituted heteroarylalkyl, optionally substituted alkaryl, optionally substituted alkylheteroaryl and polymer chains wherein the substituents are independently selected from the group consisting of alkyleneoxidyl (epoxy), hydroxy, alkoxy, acyl, acyloxy, formyl, alkylcarbonyl, carboxy, sulfonic acid, phosphorous containing groups such as phosphonate, phosphite and phosphate, alkoxy- or aryloxy-carbonyl, isocyanato, cyano, silyl, halo, amino, including salts and derivatives thereof. Preferred polymer chains include, but are not limited to, polyalkylene oxide, polyarylene ether and polyalkylene ether.

Some examples of monomers of general formula (XX) include, but are not limited to, maleic anhydride, N-alkylmaleimide, N-arylmaleimide, dialkyl fumarate and cyclopolymerisable monomers, acrylate and methacrylate esters, acrylic and methacrylic acid, styrene, acrylamide, methacrylamide, and methacrylonitrile, mixtures of these monomers, and mixtures of these monomers with other monomers.

Further examples of monomers of general formula (XX) include the following: methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylamino styrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropylacrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, vinyl phosphonic acid, monoacryloxyethyl phosphate, 2-(methacryloyloxy) ethyl phosphate, maleic anhydride, N-phenylmaleimide, N-butylmaleimide, N-vinylpyrrolidone, N-vinylcarbazole, butadiene, ethylene and chloroprene. This list is not exhaustive.

When selecting an anchoring polymeric segment so as to have a binding affinity for a given particulate material, it can be convenient to consider the hydrophilic/hydrophobic character of the particulate material and anchoring segment.

Those skilled in the art will appreciate that the type of monomers polymerised to form the steric stabilising polymeric segment and the anchoring polymeric segment will to a large extent determine the hydrophilic/hydrophobic character of the segment. Examples of ethylenically unsaturated monomers that might be considered by a person skilled in the art to give rise to hydrophilic character of the segment include, but are not limited to, acrylic acid, methacrylic acid, vinyl phosphonic acid, monoacryloxyethyl phosphate, 2-(methacryloyloxy) ethyl phosphate, hydroxyethyl methacrylate, hydroxypropyl methacrylate, acrylamide and methacrylamide, hydroxyethyl acrylate, N-methylacrylamide, dimethylaminoethyl methacrylate or vinyl pyrrolidone. Examples of ethylenically unsaturated monomers that might be considered by a person skilled in the art to give rise to hydrophobic character of the segment include, but are not limited to, vinyl acetate, methyl methacrylate, methyl acrylate, styrene, alpha-methylstyrene, butyl acrylate, butyl methacrylate, amyl methacrylate, hexyl methacrylate, lauryl methacrylate, stearyl methacrylate, ethylhexyl methacrylate, crotyl methacrylate, cinnamyl methacrylate, oleyl methacrylate, ricinoleyl methacrylate, vinyl butyrate, vinyl tert-butyrate, vinyl stearate or vinyl laurate.

When preparing the steric stabiliser by the free radical polymerisation of ethylenically unsaturated monomers, the polymerisation may require initiation from a source of free radicals. The source of initiating radicals can be provided by any suitable method of generating free radicals, such as the thermally induced homolytic scission of suitable compound(s) (thermal initiators such as peroxides, peroxyesters, or azo compounds), the spontaneous generation from monomers (e.g. styrene), redox initiating systems, photochemical initiating systems or high energy radiation such as electron beam, X- or gamma-radiation. The initiating system is chosen such that under the reaction conditions there is no substantial adverse interaction between the initiator or the initiating radicals and other reagents present.

Thermal initiators are chosen to have an appropriate half life at the temperature of polymerisation. These initiators can include one or more of the following compounds:

2,2'-azobis(isobutyronitrile), 2,2'-azobis(2-cyanobutane), dimethyl 2,2'-azobis(isobutyrate), 4,4'-azobis(4-cyanovaleric acid), 1,1'-azobis(cyclohexanecarbonitrile), 2-(t-butylazo)-2-cyanopropane, 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine) dihydrochloride, 2,2'-azobis(2-amidinopropane) dihydrochloride, 2,2'-azobis(N,N'-dimethyleneisobutyramidine), 2,2'-azobis{2-methyl-N-[1,1-bis(hydroxymethyl)-2-hydroxyethyl]propionamide}, 2,2'-azobis{2-methyl-N-[1,1-bis(hydroxymethyl)-2-ethyl]propionamide}, 2,2'-azobis[2-methyl-N-(2-hydroxyethyl)propionamide], 2,2'-azobis(isobutyramide) dihydrate, 2,2'-azobis(2,2,4-trimethylpentane), 2,2'-azobis(2-methylpropane), t-butyl peroxyacetate, t-butyl peroxybenzoate, t-butyl peroxyneodecanoate, t-butylperoxy isobutyrate, t-amyl peroxypivalate, t-butyl peroxypivalate, diisopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite. This list is not exhaustive.

Photochemical initiator systems are chosen to have the requisite solubility in the reaction medium and have an appropriate quantum yield for radical production under the conditions of the polymerisation. Examples include benzoin derivatives, benzophenone, acyl phosphine oxides, and photo-redox systems.

Redox initiator systems are chosen to have the requisite solubility in the reaction medium and have an appropriate rate of radical production under the conditions of the polymerisation; these initiating systems can include, but are not limited to, combinations of the following oxidants and reductants:

oxidants: potassium, peroxydisulfate, hydrogen peroxide, t-butyl hydroperoxide.

reductants: iron (II), titanium (III), potassium thiosulfite, potassium bisulfite.

Other suitable initiating systems are described in recent texts. See, for example, Moad and Solomon "the Chemistry of Free Radical Polymerisation", Pergamon, London, 1995, pp 53-95.

Suitable initiators which have an appreciable solubility in a hydrophilic reaction medium such as water include, but are not limited to, 4,4-azobis(cyanovaleric acid), 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine), 2,2'-azobis(N,N'-dimethyleneisobutyramidine) dihydrochloride, 2,2'-azobis(2-amidinopropane) dihydrochloride, 2,2'-azobis{2-methyl-N-[1,1-bis(hydroxymethyl)-2-ethyl]propionamide}, 2,2'-azobis[2-methyl-N-(2-hydroxyethyl) propionamide], 2,2'-azobis(isobutyramide) dihydrate, and derivatives thereof.

Suitable initiators which have an appreciable solubility in a hydrophobic reaction medium may vary depending on the polarity of the reaction medium, but typically would include oil soluble initiators such as azo compounds exemplified by the well known material 2,2'-azobisisobutyronitrile. Other readily available initiators are acyl peroxides such as acetyl and benzoyl peroxide as well as alkyl peroxides such as cumyl and t-butyl peroxides. Hydroperoxides such as t-butyl and cumyl hydroperoxides may also be used.

Compositions in accordance with the invention may be used to facilitate obtaining an image of a region of interest of a subject.

By "region of interest" is meant the entire subject or a particular area or portion of the subject. For imaging purposes, a region of interest of a subject will generally be an internal region of the subject.

An image of a region of interest of a subject will generally be obtained using a diagnostic imaging technique. By "diagnostic imaging" is meant an imaging technique that may be used to identify or determine the presence of a disease or other condition in a subject. Suitable diagnostic imaging techniques include, but are not limited to, ultrasound, X-ray, Computed Tomography (CT), Single Photon Emission Computed Tomography (SPECT), Positron Emission Tomography (PET) and Magnetic Resonance Imaging (MRI) techniques.

When used in diagnostic imaging, the compositions in accordance with the invention will typically comprise as the particulate material a diagnostic agent. By "diagnostic agent" is meant any agent which may be used in connection with obtaining a diagnostic image of a selected region of a subject for the purpose of determining the presence or otherwise of a disease or other condition in a subject. Suitable diagnostic agents include, but are not limited to, contrast agents and radioactive isotopes.

Compositions in accordance with the invention comprising as the particulate material a diagnostic agent may be conveniently referred to as a "diagnostic composition".

A preferred diagnostic composition in accordance with the invention comprises a contrast agent or radioactive isotope in the form of, or as part of, the particulate material. Preferred contrast agents include, but are not limited to, metal oxides, more preferably paramagnetic or superparamagnetic metal oxides. In a particularly preferred embodiment, the metal oxide is iron oxide. Examples of radioactive isotopes that may be used as, or as part of, a diagnostic agent include $^{99m}$Tc, $^{67}$Ga, $^{64}$Cu, $^{89}$Zr and $^{18}$F.

In diagnostic compositions in accordance with the invention comprising a metal oxide contrast agent as, or as part of, the particulate material, the liquid carrier is preferably an aqueous liquid carrier, the steric stabilising polymeric segment of the steric stabiliser preferably comprises a polymeric segment selected from polyacrylamide, polyethylene oxide, polyhydroxyethylacrylate, poly N-isopropylacrylamide, polydimethylaminoethylmethacrylate, polyvinyl pyrrolidone and copolymers thereof, and the anchoring polymeric segment of the steric stabiliser preferably comprises a polymeric segment selected from polyacrylic acid, polymethacrylic acid, polydimethylaminoethylmethacrylate and copolymers thereof.

Upon administration to a subject, diagnostic compositions in accordance with the invention comprising a contrast agent or radioactive isotope as, or as part of, the particulate material are expected to give rise to a prolonged systemic half-life of the contrast agent. In particular, it is believed that the particulate material will be maintained in a dispersed state throughout the in vivo liquid carrier by the steric stabiliser and be less prone to deleterious dilution and liquid environment effects as hereinbefore described.

In one embodiment, the composition in accordance with the invention is for diagnostic imaging, wherein the particulate material of the composition is a diagnostic agent.

In a further embodiment, there is provided use of composition in accordance with the invention for diagnostic imaging, wherein the particulate material of the composition is a diagnostic agent.

In another embodiment, there is provided a method of obtaining a diagnostic image of a region of interest of a subject, the method comprising administering a composition according to the invention to the subject and using a diagnostic imaging technique to obtain the image of said region of interest, wherein the particulate material of the composition is a diagnostic agent.

In a further embodiment, there is provided use of a composition in accordance with the invention in the manufacture of a formulation for obtaining a diagnostic image, wherein the particulate material of the composition is a diagnostic agent.

Where the particulate material used in compositions of the invention is magnetic, the compositions can advantageously be used in therapeutic treatments such as hyperthermia therapy. Hyperthermia therapy has been proposed as a treatment of diseased tissue. There is evidence to suggest that hyperthermia is effective in treating diseases, including cancerous growths. The therapeutic benefit of hyperthermia therapy is believed to be mediated through two principle mechanisms. Firstly, hyperthermia therapy has a direct tumouricidal effect on tissue by raising temperatures to greater than about 41 or 42° C. resulting in irreversible damage to cancer cells. Secondly, hyperthermia is known to sensitise cancer cells to the effects of radiation therapy and to certain chemotherapeutic drugs.

In contrast to radiotherapy or chemotherapy, hyperthermia therapy is not prone to any cumulative toxicity effects.

Nevertheless, where the particulate material is or comprises a radioactive isotope, compositions in accordance with the invention may be used for radiation therapy (also referred herein to as radiotherapy).

In the case of hyperthermia or radiation therapy, the compositions are generally administered in such a way as to cause the particulate material to concentrate in a target site. For example, the composition may be administered via intratumoral, peritumoral, or intravascular, intravenous, intraperitoneal, subcutaneous, intrahecal injection or superficial applications. For hyperthermia therapy, the compositions are preferably administered via the arterial or venous blood supply.

The compositions in accordance with the invention may be used to provide hyperthermia or radiation therapy on a target site of interest in a subject.

As used herein, a "target site of interest in a subject" is intended to mean a region of the subject that is considered to warrant hyperthermia or radiation therapy. The target site will generally be diseased tissue, such as cancerous tissue.

In order to promote the hyperthermia therapy, at least the target site is exposed to a magnetic field of clinically acceptable frequency and strength that causes the magnetic particles to radiate heat at the target site. By a magnetic field of a "clinically acceptable frequency and strength" is meant a magnetic field that will not result in unacceptable or undesirable physiological response in the subject being treated, be it from the magnetic field per se or its effect on the magnetic particles to radiate heat.

Generally, the magnetic field employed will be an alternating or AC magnetic field.

In one embodiment, the composition in accordance with the invention is for hyperthermia therapy, wherein the particulate material of the composition is magnetic.

In a further embodiment, there is provided use of composition in accordance with the invention for hyperthermia therapy, wherein the particulate material of the composition is magnetic.

In another embodiment, there is provided a method of performing hyperthermia therapy on a target site of interest in a subject, the method comprising administering a composition according to the invention to the subject and exposing at least the target site to a magnetic field of clinically acceptable frequency and strength to promote the hyperthermia therapy, wherein the particulate material of the composition is magnetic.

In a further embodiment, there is provided use of a composition in accordance with the invention in the manufacture of a formulation for performing hyperthermia therapy, wherein the particulate material of the composition is magnetic.

In another embodiment, the composition in accordance with the invention is for radiation therapy, wherein the particulate material of the composition comprises one or more radioactive isotopes.

In a further embodiment, there is provided use of composition in accordance with the invention for radiation therapy, wherein the particulate material of the composition comprises one or more radioactive isotopes.

In another embodiment, there is provided a method of performing radiation therapy on a target site of interest in a subject, the method comprising administering a composition according to the invention to the subject, wherein the particulate material of the composition comprises one or more radioactive isotopes.

In a further embodiment, there is provided use of a composition in accordance with the invention in the manufacture of a formulation for performing radiation therapy, wherein the particulate material of the composition comprises one or more radioactive isotopes.

To facilitate or enhance diagnostic or therapeutic applications of compositions in accordance with the invention, the particulate material may also have bound to its surface, and/or the steric stabiliser may comprise as a substituent, one or more ligands to target delivery of the particulate material within a subject. By a "ligand" in this context is meant a molecule that binds to or interacts with a target molecule or cell of the subject. For example, the ligand can be a small molecule, hormone, growth factor, steroid, protein, antibody, antibody fragment, peptide or polypeptide, or mimetic thereof. Thus, the ligand may be a molecule that can bind to a receptor expressed on the surface of a target cell or, conversely, to a molecule expressed on the surface of a target cell. The specific chemical composition of the ligand will be primarily selected based on the disease state or condition to be diagnosed or treated.

Targets to which the ligand can be selected to bind with include a wide variety of molecules including for example, cell signalling molecules, antibodies and antibody fragments, proteins and cell surface receptors.

By providing the particulate material and/or the steric stabiliser with one or more ligands to target delivery of the particulate material, it has been shown that particulate material such as magnetic particles can not only target cells but also be endocytosed by the cells. Those skilled in the art will appreciate that endocytosed magnetic particles can be used in effective and efficient hyperthermic treatments.

Compositions in accordance with the invention comprising such ligands may be particularly useful in diagnostic or therapeutic applications.

The invention will now be described with reference to the following examples which illustrate some preferred embodiments of the invention. However, it is to be understood that the particularity of the following description is not to supersede the generality of the proceeding description of the invention.

EXAMPLES

Example 1

Steric Stabilization of Iron Oxide Nanoparticles in Aqueous Dispersion using poly(acrylic acid)$_{10}$-block-poly(acrylamide)$_{20}$ macro RAFT agent Part (a): Preparation of Diluted Aqueous Ferrofluid Stable in Acidic Medium.

Magnetite nanoparticles were produced following the method of Massart (*Preparation of aqueous magnetic liquids in alkaline and acidic media*. IEEE Transactions on Magnetics, 1981. MAG-17(2): p. 1247-1248). In a typical reaction, 80 ml of 1M $FeCl_3.6H_2O$ in 2M HCl and 40 ml of 1M $FeCl_2.4H_2O$ in 2M HCl were mixed in a 2 Liter beaker and the mixture diluted to 1.2 Liter with MQ-water. 250 ml of $NH_4OH$ (28% (w/w)) was then quickly added to the beaker and the mixture vigorously stirred for 30 minutes. Upon adding $NH_4OH$, the colour of the mixture immediately turned from orange to black suggesting the formation of magnetite. Magnetite was then oxidized in acidic medium to maghemite by heating at 90° C. with iron nitrate for about an hour. The color of the suspension changed from black to reddish brown. Maghemite particles were then magnetically decanted, washed with acetone and finally peptized in water yielding a stable dispersion (5 wt %). The pH of the dispersion was about 1.5-2.

Part (b): Preparation of a poly(acrylic acid)$_{10}$-block-poly (acrylamide)$_{20}$ macro-RAFT agent using 2-{[butylsulfanyl) carbonothioyl]-sulfanyl}propanoic acid.

A solution of 2-{[butylsulfanyl)carbonothioyl]-sulfanyl}propanoic acid (0.75 g, 3.1 mmol), 4,4'-azobis(4-cyanovaleric acid) (0.05 g, 0.17 mmol), acrylamide (4.48 g, 63 mmol) in dioxane (18 g) and water (9 g) was prepared in a 100 mL round bottom flask.

This was stirred magnetically and sparged with nitrogen for 15 minutes. The flask was then heated at 80° C. for 2 hrs. At the end of this period, acrylic acid (2.27 g, 31 mmol) and 4,4'-azobis(4-cyanovaleric acid) (0.05 g, 0.17 mmol) were added to the flask. The mixture was deoxygenated and heating was continued at 80° C. for a further 3 hours. The copolymer solution had 21.8% solids. It was then diluted with MQ water to 0.7 wt % and the pH of the diluted copolymer solution was adjusted to 5 using 0.1M NaOH.

Part (c): Preparation of Sterically Stabilized Iron Oxide Nanoparticles from the Aqueous Ferrofluid of Part (a) and the macro-RAFT Agent of Part (b).

Nanoparticle dispersion prepared in part (a) (40 g) was diluted to 200 g with MQ water to yield 1 wt % dispersion of the nanoparticles. The pH of this nanoparticle dispersion was then raised to 5 using 0.1 M sodium hydroxide. Macro-RAFT copolymer solution from Example 1, part (b) (100 g) was then added. The mixture was vigorously stirred for 2 hours at room temperature. The nanoparticle dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solids loading in the aqueous ferrofluid dispersion to about 70 wt %. The resulting aqueous ferrofluid was found to be stable in a 60% ammonium nitrate solution.

Example 2

Steric Stabilization of Iron Oxide Nanoparticles in Aqueous Dispersion Using poly(acrylic acid)$_{10}$-block-poly(NIPAM)$_{20}$ macro RAFT Agent Part (a): Preparation of a poly(acrylic acid)$_{10}$-block-poly (NIPAM)$_{20}$ macro-RAFT Agent using 2-{[butylsulfanyl)carbonothioyl]-sulfanyl}propanoic Acid.

A solution of 2-{[butylsulfanyl)carbonothioyl]-sulfanyl}propanoic acid (0.55 g, 2.3 mmol), 4,4'-azobis(4-cyanovaleric acid) (0.03 g, 0.11 mmol), n-isopropylacrylamide (5.27 g, 46 mmol) in dioxane (15 g) and water (7.5 g) was prepared in a 100 mL round bottom flask. This was stirred magnetically and sparged with nitrogen for 15 minutes. The flask was then heated at 80° C. for 2 hrs. At the end of this period, acrylic acid (1.67 g, 23 mmol) and 4,4'-azobis(4-cyanovaleric acid) (0.03 g, 0.11 mmol) were added to the flask. The mixture was deoxygenated and heating was continued at 80° C. for a further 3 hours. The copolymer solution had 32% solids. It was then diluted with MQ water to 0.52 wt %. The pH of the diluted copolymer solution was adjusted to 5 using 0.1M NaOH.

Part (b): Preparation of Sterically Stabilized Iron Oxide Nanoparticles from the Aqueous Ferrofluid of Example 1 Part (a) and the macro-RAFT Agent of Example 2 Part (a).

Nanoparticle dispersion prepared in example 1 part (a) (40 g) was diluted to 200 g with MQ water to yield a 1 wt % dispersion of the nanoparticles and the pH of adjusted to 5 using 0.1 M sodium hydroxide solution. Macro-RAFT copolymer solution from part (a) (100 g) was then added. The mixture was vigorously stirred for 2 hours at room temperature. At this pH the copolymer is partially neutralized while the nanoparticles are sufficiently above their point of zero charge to also be stable. The nanoparticle dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solid loading in the aqueous ferrofluid dispersion to about 70 wt %. The resulting aqueous ferrofluid was found to be stable in 1M sodium chloride solution.

Example 3

Steric Stabilization of Iron Oxide Nanoparticles in Aqueous Dispersion Using a Poly(acrylic acid)$_{10}$-block-poly(ethylene oxide)$_{17}$ macro RAFT Agent Part (a): Esterification of poly(ethylene glycol) monomethyl ether with 2-{[(butylsulfanyl)carbonothioyl] sulfanyl}propanoic acid MethoxyPEG (Mn ~798) was warmed and stirred to liquefy and homogenize it, and 19.95 g (25.0 mmol) was then weighed into a 250 mL 3-necked round bottom flask, and then allowed to solidify. 2-{[(butylsulfanyl)carbonothioyl] sulfanyl}propanoic acid (6.96 g, 29.3 mmol) and 4-dimethylaminopyridine (360 mg, 2.9 mmol) were added to the flask, a magnetic stirbar was introduced, and the flask was purged with nitrogen. Dry dichloromethane (75 mL) was added and the mixture was stirred until the solids had all dissolved. The flask was then cooled in an ice bath and a solution of N,N'-dicyclohexylcarbodiimide (6.03 g, 29.3 mmol) in dry dichloromethane (25 mL) was then added dropwise over 1 h. The reaction was stirred in the ice-bath for a further 10 min, then at room temperature for 24 h. The resulting yellow slurry was diluted with 1:1 hexane-ether (100 mL) and filtered through a sintered glass funnel. The filter residue was washed with further small portions of 1:1 hexane-ether until it was white, and the combined filtrates were evaporated to give a cloudy and gritty dull orange oil. The crude product was dissolve in dichloromethane (75 mL) and stirred with solid oxalic acid (4 g) for 1 h, then diluted with hexane (70 mL) and allowed to settle, producing a flocculent white precipitate. The mixture was filtered and evaporated, and the crude oil was dissolved in 2:1 hexane-dichloromethane (150 mL) and passed through a plug of alumina (40 g). Elution with further 2:1 hexane-dichloromethane was continued until the eluate was colourless. The combined eluates were dried with sodium sulfate, filtered, and evaporated to give a clear pale orange oil, 24.69 g, 97%.

Part (b): Preparation of a poly(acrylic acid)$_{10}$-block-poly(ethylene oxide)$_{17}$ macro-RAFT Agent Using the Polyethylene Oxide Based RAFT Agent Prepared in Example 3, Part (a).

A solution of macro-RAFT from example 3 part(a) (2.0 g, 1.9 mmol), acrylic acid (1.41 g, 19 mmol), 4,4'-azobis(4-cyanovaleric acid) (0.03 g, 0.11 mmol) in dioxane (7.5 g) and water (3.75 g) was prepared in a 100 mL round bottom flask. This was stirred magnetically and sparged with nitrogen for 15 minutes. The flask was then heated at 80° C. for 2 hrs. The resulting copolymer solution had 23.7% solids. The solution was then diluted to 0.29 wt % with MQ water. The pH of the diluted copolymer solution was adjusted to 5 with 0.1M NaOH.

Part (c): Preparation of Sterically Stabilized Iron Oxide Nanoparticles from the Aqueous Ferrofluid of Example 1 Part (a) and the macro-RAFT agent of Example 3 Part (b).

Nanoparticle dispersion prepared in example 1 part (a) (5 wt %, 40 g) was diluted to 200 g with MQ water to yield 1 wt % dispersion of the nanoparticles and the pH adjusted to 5 using 0.1 M sodium hydroxide solution. Macro-RAFT copolymer solution from example 3 part (b) (0.29 wt %, 100 g) was then added. The mixture was vigorously stirred for 2 hours at room temperature. At this pH the copolymer is partially neutralized while the nanoparticles are sufficiently above their point of zero charge to also be stable. The resulting dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solids loading in the aqueous ferrofluid dispersion to about 70 wt %. The resulting aqueous ferrofluid was found to be stable in 1M sodium chloride solution.

Example 4

Steric Stabilization of Iron Oxide Nanoparticles in Aqueous Dispersion Using poly(monoacryloxyethyl phosphate)$_{10}$-block-poly(ethylene oxide)$_{17}$ macro RAFT Agent and Based on the poly(ethylene oxide) RAFT Agent Prepared in Example 3, Part (a)

Part (a): Preparation of a poly(monoacryloxyethyl phosphate)$_{10}$-block-poly(ethylene oxide)$_{17}$ macro RAFT Agent Using the Polyethylene Oxide Based RAFT Agent Prepared in Example 3, PART (a).

A solution of macroRAFT (1.0 g, 0.9 mmol) from example 3 part(a), monoacryloxyethyl phosphate (1.92 g, 9.8 mmol), 4,4'-azobis(4-cyanovaleric acid) (0.018 g, 0.06 mmol) in dioxane (15 g) and water (7.5 g) was prepared in a 100 mL round bottom flask. This was stirred magnetically and sparged with nitrogen for 15 minutes. The flask was then heated at 80° C. for 2 hrs. The copolymer solution had 11.5% solids. It is then diluted with MQ water to 1.2 wt %. The pH of the diluted copolymer solution was adjusted to 5 with 0.1M NaOH.

Part (b): Preparation of Sterically Stabilized Iron Oxide Nanoparticles from the Aqueous Ferrofluid of Example 1 Part (a) and the macro-RAFT Agent of Example 4 Part (a).

40 g of the nanoparticle dispersion (5 wt %) prepared in Example 1, part (a) was diluted with MQ water to 200 g to yield 1 wt % dispersion of the nanoparticles. The pH of this prepared nanoparticle dispersion was then raised to 5. A 100 g 1.2 wt % solution of the Macro-RAFT copolymer, also at pH 5, from example 4 part (a) was then added to a 1 wt % dispersion of iron oxide maintained at the same pH. The mixture was vigorously stirred for 2 hours at room temperature. At this pH the copolymer is partially neutralized while the nanoparticles are sufficiently above their point of zero charge to also be stable. Phosphate ions from the poly (monoacryloxyethyl phosphate) block of the copolymer chemically adsorbed onto the particle surface yielding a stable sterically stabilized dispersion of nanoparticles in water. The dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solids loading in the aqueous ferrofluid dispersion to about 70 wt %. The resulting aqueous ferrofluid was found to be stable in phosphate buffered saline (PBS) solution.

Example 5

Targeting Iron Oxide Nanoparticles of Example 1-Part(c) to Ovarian Cancer Cells In Vitro Part (a): Preparation of Folate-N-Hydroxysuccinimide ester To anhydrous DMSO (20 ml) triethylamine (0.5 ml) and Folate (1 gram) were added in order. Once a clear solution was obtained, further additions of N hydroxysuccinimide (NHS, 0.52 g) and 1,3-Dicyclohexylcarbodiimide (DCC, 0.70 g) were made in order. The resulting solution was stirred in the dark at room temperature overnight. The precipitated side product, dicyclohexylurea, was removed by centrifugation and filtration of the supernatant. The solution was stored at 4° C.

Part (b): Modification of Stabilisers for Iron Oxide Particles of Example 1-Part (c)

Into coated nanoparticles prepared from Example 1-Part (c) (7.8 g) NHS (14.4 mg) and then 1-Ethyl-3-(3-Dimethylamino-propyl)carbodiimide (EDAC, 20 mg) were added, mixed by shaking and allowed to react for 2 hours at room temperature. A solution of diamine (90 mg of 2,2'-(Ethylenedioxy)bis-(ethylamine) in 1 ml of water) was then added to the reaction mixture and allowed to react for a further 3.5 hours. The solution was then dialysed against excess water with numerous changes, to remove free EDAC and the reaction by-products.

Part (c): Conjugation of Fluorescein Isothiocyanate (FITC) to Iron Oxide Nanoparticles of Example 5-Part(b)

The magnetic nanoparticles of Example 5-Part (b) (3.3 ml) were adjusted to pH 8.0 using sodium hydroxide solution. 0.044 ml of FITC solution (7.3 mg/ml of water) was then added. The sample was mixed rapidly without magnetic stirring, and incubated in the dark overnight. The product was dialysed against Milli Q water until free unbound FITC could no longer be detected.

Part (d): Conjugation of Fluorescein Isothiocyanate (FITC) and Folate Ester of Part (a) to Iron Oxide Nanoparticles of Example 5-Part (b)

The particles of Example 5-Part (b) (3.3 ml) were adjusted to pH 8.0 using sodium hydroxide solution. 0.044 ml of FITC solution (7.3 mg/ml of water) and folate ester solution of Part (a) (86 mg) was then added. The sample was mixed rapidly without magnetic stirring, and incubated in the dark overnight. The product was dialysed against Milli Q water until free unbound FITC could no longer be detected.

Part (e): Target Iron Oxide Nanoparticles of Part (c) and (d) to Human Ovarian Cancer Cells A2780s In Vitro A2780 cells were maintained as monolayers in Dulbecco's modified Eagle's medium (DMEM), supplemented with 5% foetal calf serum, 2 mM glutamine, and 100 μg/ml penicillin/streptomycin, in a humidified 37° C. incubator with 5% $CO_2$. Cells were seeded onto 22 mm glass cover slips in 6 well flasks at a density of ~$2 \times 10^5$ cells per well. After 24 hours, the monolayers were washed three times with phosphate buffered saline (PBS, pH 7.4), then cultured in folate-free RPMI medium (Invitrogen) supplemented with 5% foetal calf serum, 2 mM glutamine, and 100 μg/ml penicillin/streptomycin. After a further 18-24 hours, the cells were washed with the PBS three times, then incubated with 1 ml solution of the nanoparticles in folate free RPMI solution (1 ml of the nanoparticles of Part (c) or (d) in 2.5 ml of RPMI solution) in a humidified 37° C. incubator with 5% $CO_2$ for 2 hours. The cells were then washed 3 times with PBS, and fixed using a fresh solution of 4% paraformaldehyde in PBS for 10 minutes at room temperature. The cells were stained using syto-blue solution in PBS (concentration at ~100 nM).

The fixed cells were studied using a confocal microscopy. It was observed that substantial amounts of green fluorescence was visible inside cells treated with FITC+folate conjugated nanoparticles of Part (d), and almost none in cells treated with FITC conjugated nanoparticles of Part (c). It showed that the nanoparticles with folate as a targeting agent were endocytosed by the ovarian cancer cells A2780s.

Example 6

Intravenous Injection and Biodistribution of Magnetic Nanoparticles in a White New Zealand Rabbit by Radio Imaging Part (a): Preparation of Diluted Aqueous Ferrofluid Containing Radioactive $Ga^{67}$ into the Crystal Lattice of Iron Oxide Stable in Acidic Medium Magnetite nanoparticles were produced following the method of Massart (*Preparation of aqueous magnetic liquids in alkaline and acidic media*. IEEE Transactions on Magnetics, 1981. MAG-17(2): p. 1247-1248). In a typical reaction, 4 ml of 0.1M $FeCl_3.6H_2O$ in 2M HCl, 2 ml of 0.1 M $FeCl_2.4H_2O$ in 2M HCl and 200 Mbq of radioactive $Ga^{67}$ were mixed in a 40 ml scintillation vial and the mixture diluted to 12 ml with Mili-Q-water. 11 ml of $NH_4OH$ (28% (w/w)) was then quickly added to the beaker and the mixture vigorously stirred on the vortex mixer for 30 minutes. Upon adding $NH_4OH$, the colour of the mixture immediately turned from orange to black suggesting the formation of magnetite. Magnetite was then oxidized in acidic medium to maghemite by heating at 90° C. with iron nitrate for about an hour. The color of the suspension changed from black to reddish brown. Maghemite particles were then magnetically decanted, washed with acetone and finally peptized in water yielding a stable dispersion (0.5 wt %). The pH of the dispersion was about 1.5-2.

Part (b): Preparation of Sterically Stabilized Iron Oxide Nanoparticles from the Aqueous Ferrofluid of Example 6 Part (a) and the Macro-Raft Agent of Example 4 part (a).

10 g of the nanoparticle dispersion (0.5 wt %) prepared in Example 6, part (a) was diluted with Mili-Q water to 20 g to yield 0.25 wt % dispersion of the nanoparticles. The pH of this prepared nanoparticle dispersion was then raised to 5. A 4.5 g, 1.2 wt % solution of the macro-RAFT copolymer, also at pH 5, from example 4 part (a) was then added to a 0.5 wt % dispersion of iron oxide maintained at the same pH. The mixture was vigorously stirred for 2 hours at room temperature. At this pH the copolymer was partially neutralized while the nanoparticles were sufficiently above their point of zero charge to also be stable. Phosphate ions from the poly (monoacryloxyethyl phosphate) block of the copolymer chemically adsorbed onto the particle surface yielding a stable sterically stabilized dispersion of nanoparticles in water. The dispersion was then dialysed to remove salts, residual solvents, unwanted low molecular weight reaction side products and unbound polymer. Bigger particles in the dispersion were removed by ultracentrifugation. The purified nanoparticle dispersion was then distilled to increase the solids loading in the aqueous ferrofluid dispersion to about 0.5 wt %. The resulting aqueous ferrofluid was found to be stable in phosphate buffered saline (PBS) solution.

Part (c): Biodistribution of Magnetic Nanoparticles in the Rabbit

The magnetic nanoparticles of Example 6, Part (b) (3 ml) with the radioactivity of 1.5 milli Curies were injected into the ear vein of a 3.9 Kg New Zealand white rabbit. The nanoparticle dispersion was filtered through the 220 nm filter prior to injection. The distribution of the nanoparticles in different parts of the body was monitored with the clinical γ camera. Various parts of the body such as liver, spleen, bone marrow and also small portions of the lungs and skull were successfully imaged. Nanoparticles circulated for about 45 minutes in the body before they were taken up by parts of reticuloendothelial system. No toxicity was detected as the rabbit resumed its normal activities at the end of the experiment.

Example 7

Toxicity Studies of Sterically Stabilized Iron Oxide Nanoparticle Disperions in Rats The magnetic nanoparticles of Example 4-Part (b) were used in a toxicity test at the intended imaging dose rate and five times the intended imaging dose rate, as described below:

The acute toxicity of magnetic nanoparticles imaging agent was investigated in young adult Sprague-Dawley rats. Groups of three male and three female rats were administered a single dose of either 0.9% sterile saline vehicle control or the magnetic nanoparticles test article at a dose of 2.5 or 12.5 mg/kg. These dose levels were designed as a low dose equivalent to the intended dose rate for imaging studies and a high dose corresponding to approximately five times the intended clinical dose. The doses were administered by bolus intravenous injection into the lateral tail vein at a dose rate of 5 mL/kg. The rats were monitored for clinical signs of toxicity for the four hours immediately following dose administration and daily thereafter for a seven day observation period. Body weight measurements were also made prior to dosing and daily throughout the observation period. On study day eight the rats were weighed prior to euthanasia by carbon dioxide asphyxia. A gross necropsy was then performed which included measurement of the weights of critical organs.

The treatment with test article was not associated with clinical signs of toxicity. Incidental findings of toxicity not related to test article treatment included mild piloerection in all groups on Study Day 1 following dosing. Test article treatment was also not associated with any effects on body weight. There were no gross pathology findings or changes in organ weights associated with test article treatment.

Treatment with a single bolus intravenous injection of magnetic nanoparticles imaging agent at 2.5 and 12.5 mg/kg was well tolerated in adult male and female Sprague Dawley rats over a seven day observation period.

Example 8

Steric Stabilization of Barium Sulphate in Aqueous Dispersion Using poly(acrylic acid)$_7$-co-poly(styrene sulphonate)$_3$-block-poly(acrylamide)$_{20}$ macro-RAFT macro-RAFT Agent Part (a): Preparation of a poly(acrylic acid)$_7$-co-poly(styrene sulphonate)$_3$-block-poly(acrylamide)$_{20}$ macro-RAFT agent using 2-{[butylsulfanyl)carbonothioyl]-sulfanyl}propanoic acid.

A solution of 2-{[butylsulfanyl)carbonothioyl]-sulfanyl}propanoic acid (0.65 g, 2.7 mmol), 4,4'-azobis(4-cyanovaleric acid) (0.08 g, 0.3 mmol), acrylamide (3.87 g, 54.3 mmol) in dioxane (15 g) and water (15 g) was prepared in a 100 mL round bottom flask. This was stirred magnetically and sparged with nitrogen for 15 minutes. The flask was then heated at 80° C. for 2 hrs. At the end of this period, acrylic acid (1.68 g, 23.3 mmol), 4-styrene sulphonic acid (1.37 g, 6.6 mmol) and 4,4'-azobis(4-cyanovaleric acid) (0.05 g, 0.17 mmol) were added to the flask. The mixture was deoxygenated and heating was continued at 80° C. for a further 3 hours. The copolymer solution had 31% solids. It was then diluted with MQ water to 0.4 wt % and the pH of the diluted copolymer solution was adjusted to 2.2 using 0.1M HCl.

Part (b): Preparation of Sterically Stabilized Barium Sulphate Using the Macro-Raft agent of Example 8 part (a).

10 gram of Barium Sulphate dispersion in water (1 wt %) was taken in a 100 ml round bottom flask. The pH of the dispersion was adjusted to 2.2 using 0.1M HCl. Macro-RAFT copolymer solution from Example 8, part (a) (10 g) was then added. The mixture was vigorously stirred for 2 hours at room temperature. The nanoparticle dispersion was then dialysed to remove salts, residual solvents, unwanted low molecular weight reaction side products and unbound polymer. The dispersion so formed was stable at a pH of 2.2.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A composition suitable for administration to a subject, the composition comprising pharmacologically acceptable pre-formed solid particulate material dispersed throughout a pharmacologically acceptable liquid carrier, the particulate material having a largest dimension that is less than 0.5 microns and being maintained in the dispersed state by a steric stabilizer such that a dispersion is obtained which is stable over two weeks when diluted in a 0.15M NaCl solution, wherein the steric stabiliser is a polymeric material comprising a steric stabilising polymeric segment and an anchoring polymeric segment, one or both of which are derived from one or more ethylenically unsaturated monomers that have been polymerised by a living polymerisation technique, wherein the steric stabilising polymeric segment is different from the anchoring polymeric segment, and wherein the anchoring polymeric segment has an affinity toward the surface of the particulate material and secures the stabiliser to the particulate material, and wherein the steric stabiliser is a block copolymer having a number average molecular weight of less than 30,000.

2. The composition according to claim 1, wherein the block copolymer has a number average molecular weight ranging from about 1,000 to about 3,000.

3. The composition according to claim 1, wherein the living polymerisation technique is selected from ionic polymerisation and controlled radical polymerisation (CRP).

4. The composition according to claim 1, wherein the anchoring polymeric segment is derived from one or more ethylenically unsaturated monomers that have been polymerised by reversible addition fragmentation chain transfer (RAFT) polymerisation.

5. The composition according to claim 1, wherein the steric stabilising polymeric segment comprises polyacrylamide, polyethylene oxide, polyhydroxyethylacrylate, poly N-isopropylacrylamide, polydimethylamino-ethylmethacrylate, polyvinyl pyrrolidone or a copolymer thereof.

6. The composition according to claim 1, wherein the steric stabilising polymeric segment has no more than 50 polymerised monomer units that collectively form the segment.

7. The composition according to claim 1, wherein the anchoring polymeric segment comprises a polymerised residue of one or more ionisable monomers.

8. The composition according to claim 7, wherein the ionisable monomers are selected from methacrylic acid, acrylic acid, itaconic acid, p-styrene carboxylic acids, p-styrene sulfonic acids, vinyl sulfonic acid, vinyl phosphonic acid, monoacryloxyethyl phosphate, 2-(methacryloyloxy) ethyl phosphate, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, and 3-(diethyl amino) ethyl and propyl acrylates and methacrylates.

9. The composition according to claim 1, wherein the anchoring polymeric segment comprises polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, poly-3-(diethyl amino) ethyl and propyl acrylates and methacrylates, polydimethylaminoethyl-methacrylate, or a copolymer thereof.

10. The composition according to claim 1, wherein the anchoring polymeric segment has no more than 50 polymerised monomer units that collectively form the segment.

11. The composition according to claim 1, wherein the anchoring polymeric segment comprises at least 5 polymerised monomer residues that each provide a site that functions to secure the stabiliser to the particulate material.

12. The composition according to claim 1, wherein the particulate material comprises a pharmaceutically active compound, a metal, a metal alloy, a metal salt, a metal complex, a metal oxide, a radioactive isotope or combinations thereof.

13. The composition according to claim 1, wherein the particulate material comprises gold, silver or a salt, complex or oxide thereof, calcium carbonate, barium sulphate, iron oxide, chromium oxide, cobalt oxide, manganese oxide, iron oxyhydroxide, chromium oxyhydroxide, cobalt oxyhydroxide, manganese oxyhydroxide, chromium dioxide, one or more radioactive isotopes selected from an Auger-electron emitter, an alpha emitter and a beta emitter, or combinations thereof.

14. The composition according to claim 1, wherein the particulate material is magnetic.

15. The composition according to claim 14, wherein the magnetic particulate material comprises magnetite ($Fe_3O_4$), maghemite ($\gamma$-$Fe_2O_3$) or a combination thereof.

16. The composition according to claim 1, wherein the liquid carrier comprises water, petroleum oil, animal oil, vegetable oil, mineral oil, methylene glycol, propylene glycol, polyethylene glycol, polypropylene glycol, ethanol, isopropyl alcohol, benzyl alcohol or combinations thereof.

17. The composition according to claim 1, wherein the particulate material and/or the steric stabiliser comprises one or more ligands that is capable of binding with a target molecule or cell of the subject.

18. The composition according to claim 1, wherein the particulate material comprises a radioactive isotope.

19. A method of obtaining a diagnostic image of a region of interest of a subject, the method comprising administering a composition according to claim 1 to the subject and using a diagnostic imaging technique to obtain the image of said region of interest, wherein the particulate material of the composition is a diagnostic agent.

20. A method of performing hyperthermia therapy on a target site of interest in a subject, the method comprising administering a composition according to claim 1 to the subject and exposing at least that target site to a magnetic field of clinically acceptable frequency and strength to promote the hyperthermia therapy, wherein the particulate material of the composition is magnetic.

21. A method of performing radiation therapy on a target site of interest in a subject, the method comprising administering a composition according to claim 1 to the subject, wherein the particulate material of the composition comprises one or more radioactive isotopes.

22. The process of using a composition according to claim 1 in a method of performing hyperthermia and/or radiation therapy, the method comprising administering the composition of claim 1 to a subject.

23. The process of using a composition according to claim 1 in a method of obtaining a diagnostic image of a region of interest of a subject, the method comprising administering the composition of claim 1 to the subject.

* * * * *